(12) United States Patent
Stave et al.

(10) Patent No.: US 6,663,833 B1
(45) Date of Patent: Dec. 16, 2003

(54) INTEGRATED ASSAY DEVICE AND METHODS OF PRODUCTION AND USE

(75) Inventors: James W. Stave, Elkton, MD (US); George B. Teaney, III, Oxford, PA (US); Werner Kroll, Solingen (DE)

(73) Assignees: Strategic Diagnostics Inc., Newark, DE (US); Bayer AG, Leverkusen (DE)

( * ) Notice: Subject to any disclaimer, the term of this patent is extended or adjusted under 35 U.S.C. 154(b) by 0 days.

(21) Appl. No.: 09/263,183

(22) Filed: Mar. 5, 1999

Related U.S. Application Data

(60) Provisional application No. 60/077,453, filed on Mar. 10, 1998.

(51) Int. Cl.[7] .............................................. G01N 21/00
(52) U.S. Cl. ..................... 422/81; 422/58; 422/68.1; 422/56; 422/101; 422/103; 422/110; 436/165; 436/178; 436/518; 435/286.5; 435/287.1
(58) Field of Search .................. 435/287.1, 286.5; 422/58, 70, 73, 81, 82, 101, 102, 103, 68.1, 56, 110; 436/165, 177, 178, 52, 179, 518; 366/197

(56) References Cited

U.S. PATENT DOCUMENTS

| | | | |
|---|---|---|---|
| 4,310,399 A | | 1/1982 | Columbus ............... 204/195 R |
| 4,315,754 A | * | 2/1982 | Ruzicka et al. ............... 436/52 |
| 4,756,884 A | * | 7/1988 | Hillman et al. ............... 422/73 |
| 4,859,421 A | | 8/1989 | Apicella ....................... 422/61 |
| 4,918,025 A | | 4/1990 | Grenner ...................... 436/165 |
| 4,959,324 A | | 9/1990 | Ramel et al. ............... 436/169 |
| 4,963,498 A | | 10/1990 | Hillman et al. ............. 436/169 |
| 4,987,085 A | | 1/1991 | Allen et al. ................. 436/169 |
| 4,999,287 A | | 3/1991 | Allen et al. .................... 435/11 |
| 5,039,617 A | | 8/1991 | McDonald et al. .......... 436/69 |
| 5,079,142 A | | 1/1992 | Coleman et al. ........... 435/7.92 |
| 5,087,556 A | | 2/1992 | Ertinghausen ............... 435/7.9 |
| 5,132,086 A | | 7/1992 | Allen et al. ................... 422/56 |
| 5,135,719 A | | 8/1992 | Hillman et al. ............. 422/101 |

(List continued on next page.)

FOREIGN PATENT DOCUMENTS

| | | |
|---|---|---|
| WO | WO 89/10564 | 2/1989 |
| WO | WO 93/24231 | * 12/1993 |
| WO | WO 97/22825 | 6/1997 |
| WO | WO 97/37222 | 9/1997 |

OTHER PUBLICATIONS

Getting Started in HPLC; Section 2C. HPLC Injectors—http://www.Icresources.com/courses/getting_started/2c01.htm, Apr. 2, 2001.

(List continued on next page.)

*Primary Examiner*—Long V. Le
*Assistant Examiner*—Gary Counts
(74) *Attorney, Agent, or Firm*—Kilpatrick Stockton LLP

(57) ABSTRACT

An assay device for the detection of analyte in a sample, methods and immunoassay formats for performing an assay with or without the device, and methods for manufacturing the device are provided. The device is a continuous liquid flow channel having a proximal and a distal end, with a detection membrane in fluid communication with the distal end of the flow channel. Interspersed between the assay buffer and detection membrane, and continuous with the liquid flow channel, are a sample delivery means, one or more reservoirs containing the reagents necessary for conducting the assay, and, optionally, mixing or incubation reservoirs for combining the sample and reagents. The geometry of the liquid flow channel regulates the flow rate of the liquids through the channel, thereby controlling incubation, mixing and reaction time. The preferred detection membrane is an immunochromatographic test strip containing immobilized reagents. The detection of labeled reagent in a particular area of the detection membrane reflects the presence or relative amount of analyte in the sample. Detection may be achieved visually. One or more liquid flow channels may be contained within a single housing for simultaneous, consecutive, or comparative sample analysis.

29 Claims, 5 Drawing Sheets

U.S. PATENT DOCUMENTS

| | | | |
|---|---|---|---|
| 5,147,607 A | * 9/1992 | Mochida | 422/4 |
| 5,164,598 A | 11/1992 | Hillman et al. | 250/341 |
| 5,204,063 A | 4/1993 | Allen | 422/58 |
| 5,217,905 A | 6/1993 | Marchand et al. | |
| 5,223,219 A | 6/1993 | Subramanian et al. | 422/55 |
| 5,225,163 A | 7/1993 | Andrews | 422/61 |
| 5,300,779 A | 4/1994 | Hillman et al. | 250/341 |
| 5,304,487 A | 4/1994 | Wilding et al. | 435/291 |
| 5,399,486 A | 3/1995 | Cathey et al. | 435/7.9 |
| 5,407,832 A | * 4/1995 | Hayashibe et al. | 436/74 |
| 5,422,271 A | 6/1995 | Chen et al. | 435/287 |
| 5,486,335 A | 1/1996 | Wilding et al. | 422/55 |
| 5,486,478 A | * 1/1996 | Kuriyama | 436/52 |
| 5,503,985 A | 4/1996 | Cathey et al. | 435/7.9 |
| 5,571,410 A | 11/1996 | Swedberg et al. | 210/198.2 |
| 5,605,662 A | 2/1997 | Heller et al. | 422/68.1 |
| 5,656,448 A | 8/1997 | Kang et al. | 435/7.94 |
| 5,658,531 A | 8/1997 | Cope et al. | 422/58 |
| 5,660,993 A | 8/1997 | Cathey et al. | 435/7.9 |
| 5,681,529 A | 10/1997 | Taguchi et al. | 422/61 |
| 5,698,406 A | 12/1997 | Cathey et al. | 435/7.9 |
| 5,725,831 A | 3/1998 | Reichler et al. | 422/56 |
| 5,726,026 A | 3/1998 | Wilding et al. | 435/7.21 |
| 5,731,212 A | 3/1998 | Gavin et al. | 436/526 |
| 5,736,404 A | 4/1998 | Yassinzadeh et al. | 436/52 |
| 5,744,366 A | 4/1998 | Kricka et al. | 436/63 |
| 5,750,184 A | 5/1998 | Imburgia | 427/2.13 |
| 5,750,333 A | 5/1998 | Clark | 435/5 |
| 5,783,148 A | 7/1998 | Cottingham et al. | 422/56 |
| 5,798,215 A | 8/1998 | Cathey et al. | 435/7.9 |
| 5,800,781 A | 9/1998 | Gavin et al. | 422/73 |
| 5,811,296 A | 9/1998 | Chemelli et al. | 435/287.2 |
| 5,827,681 A | 10/1998 | Krug et al. | 435/34 |

OTHER PUBLICATIONS

Kearney, et al., "A New Mouse Myeloma Cell Line That Has Lost Immunoglobulin Expression But Permits The Construction Of Antibody–Secreting Hybrid Cell Lines"—J. Immunol. 123:1548–1558 (1979).

Polin, Jenevieve Blair—"For Lab Chips, The Future Is Plastic"—IVD Technology News—pp. 12, 18–19, May/Jun. 1997.

Genesis Report—DX—vol. 6—No. 1—"Miniaturized Diagnostics Grow In Importance"—Jul. 1, 1996.

Microfabrication & Microfluidic Technologies—Advances In The Miniaturization of Bioanalytical Devices—IBC's $2^{nd}$ Annual Conference—Aug. 7–8, 1997—Itinerary.

Chemical Abstracts, vol. 123, No. 9, Aug. 28, 1995, Columbus, OH, Abstract No. 106861, XP002113707; Clark et al.; "An immunofiltration apparatus for accelerating the visualization of antigen on membrane supports"; *Analytical Biochemistry,* vol. 228, No. 2, 1995.

Chemical Abstracts, vol. 123, No. 24, Dec. 11, 1995, Columbus, OH, Abstract No. 321307, XP002113708; Teaney et al.; "Development of an enzyme immunoassay based filed screening system for the detection of RDX in soil and water"; *Proceedings of the $87^{th}$ Annual Meeting of the Air Waste Management Association,* vol. 14b, 1994, p. 94.RP143.05.

\* cited by examiner

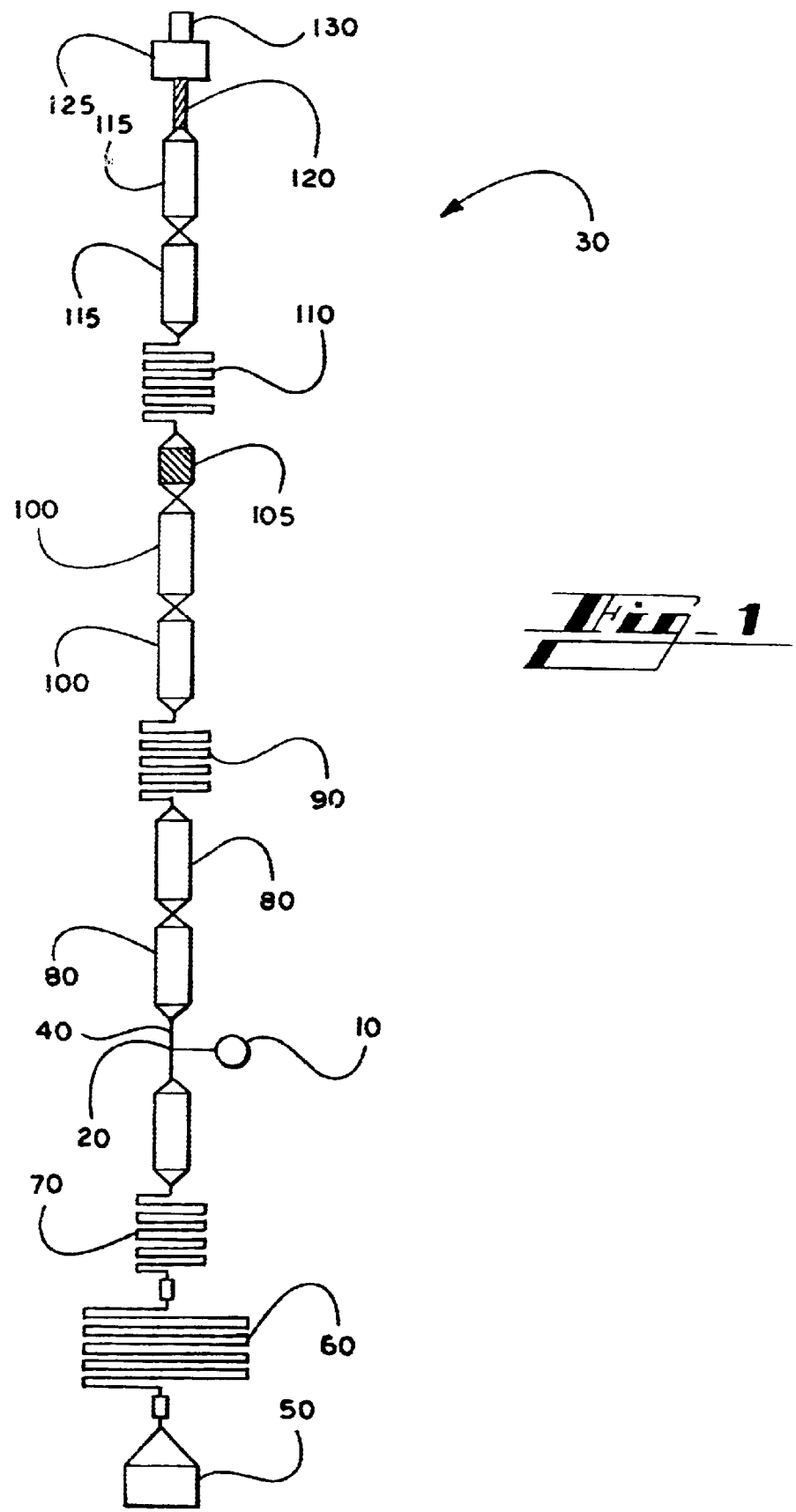

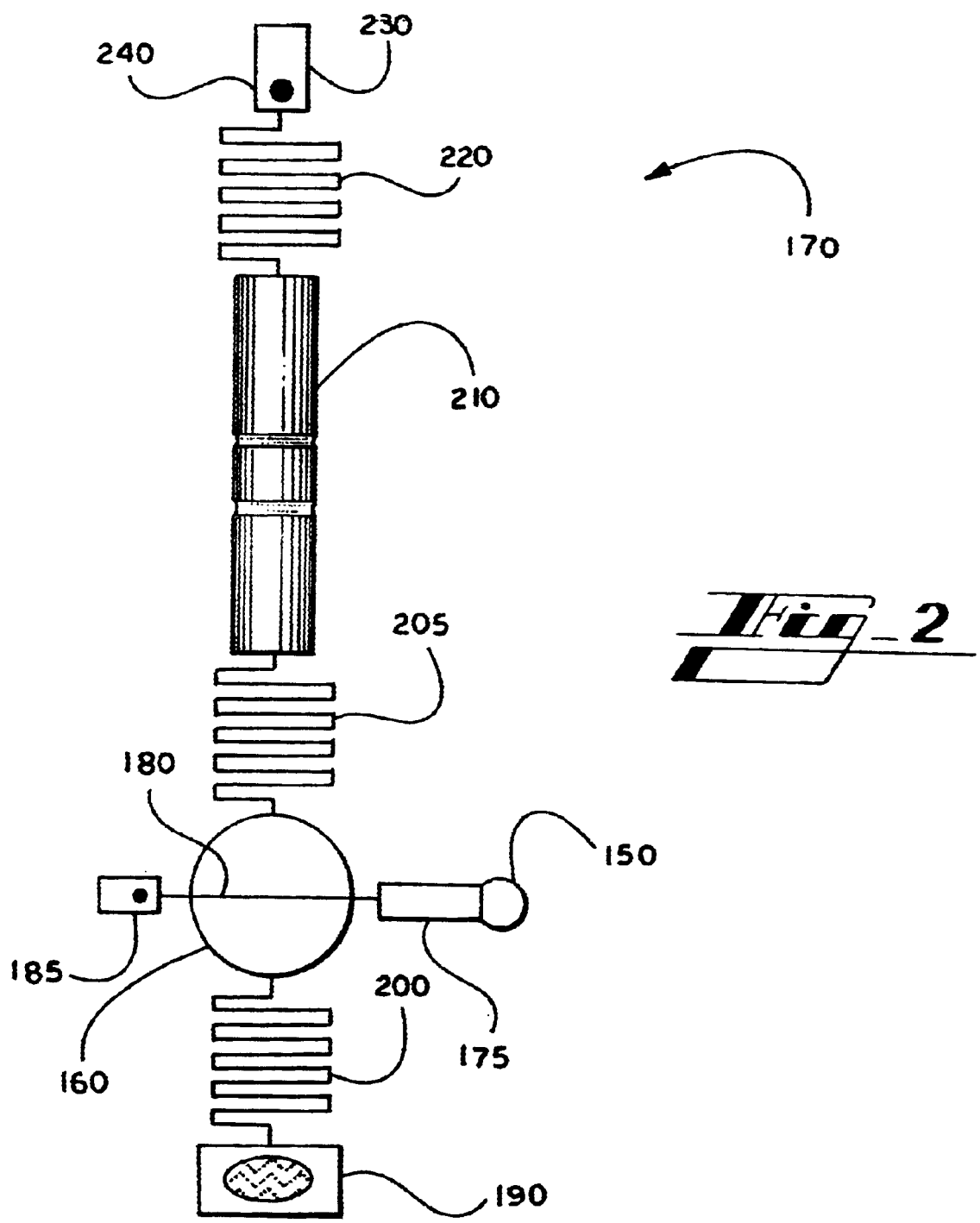
Fig_2

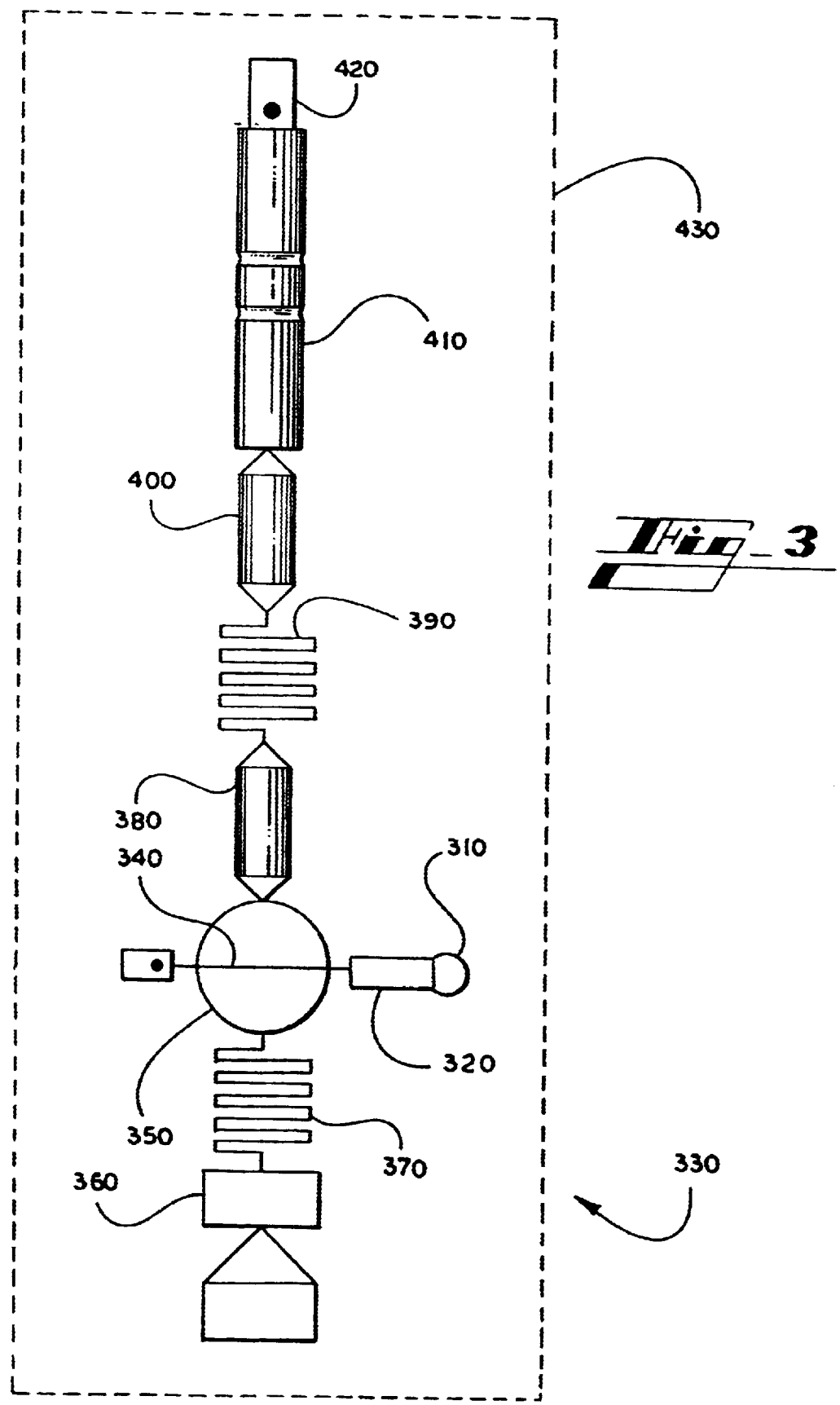
Fig_3

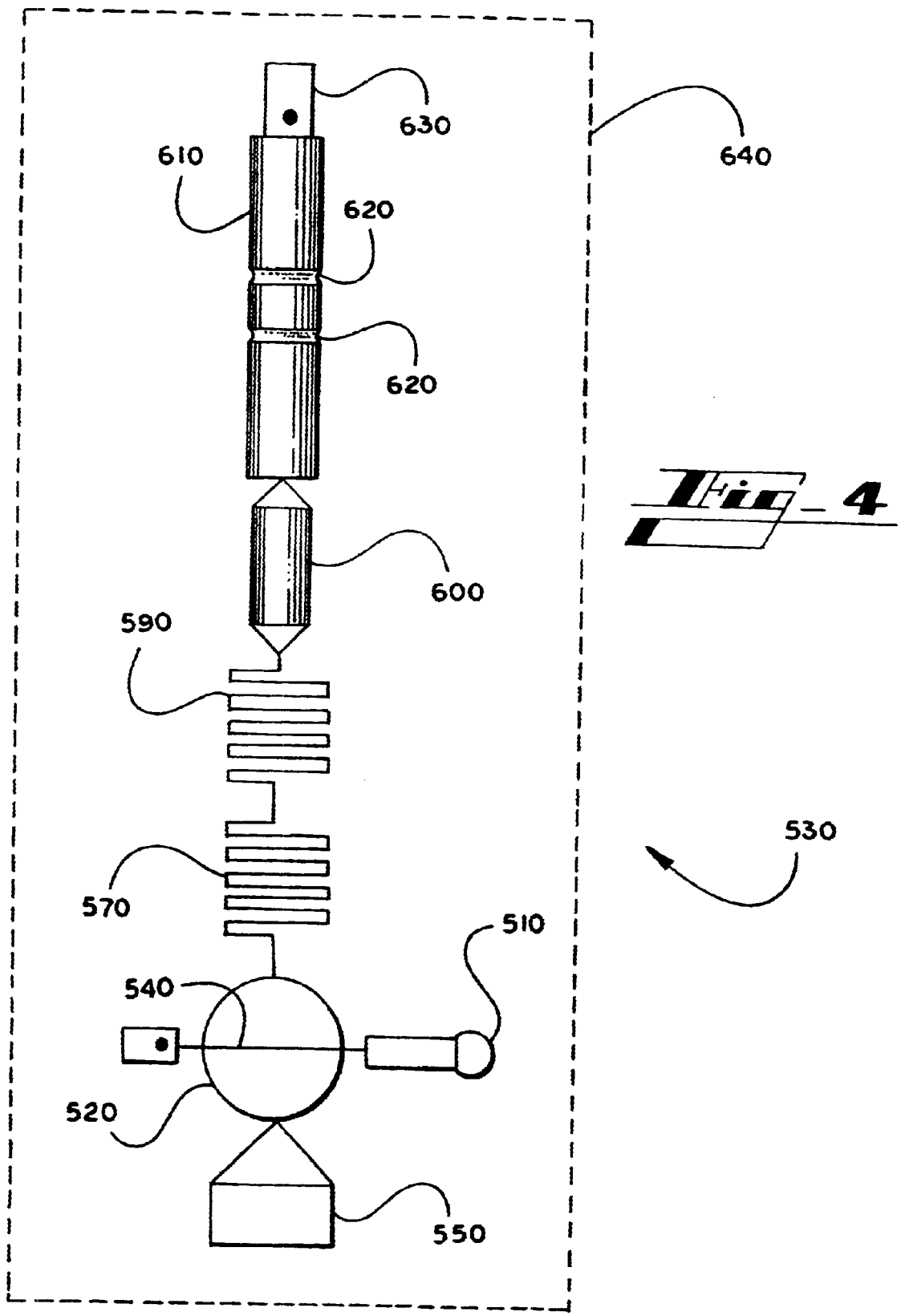
Fig_4

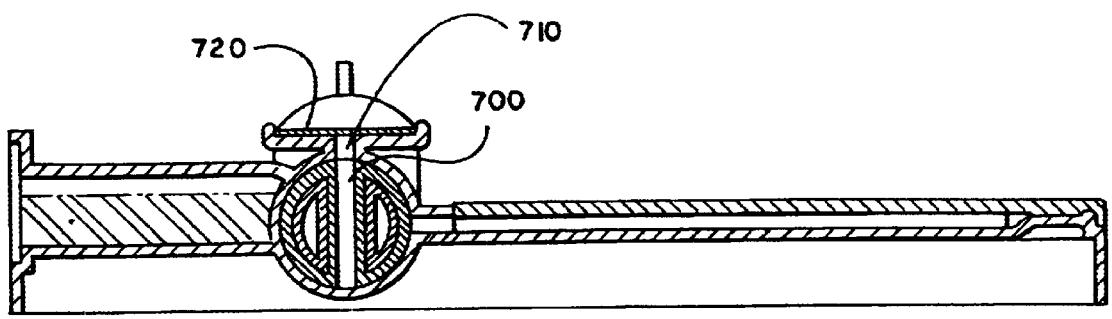
Fig_5
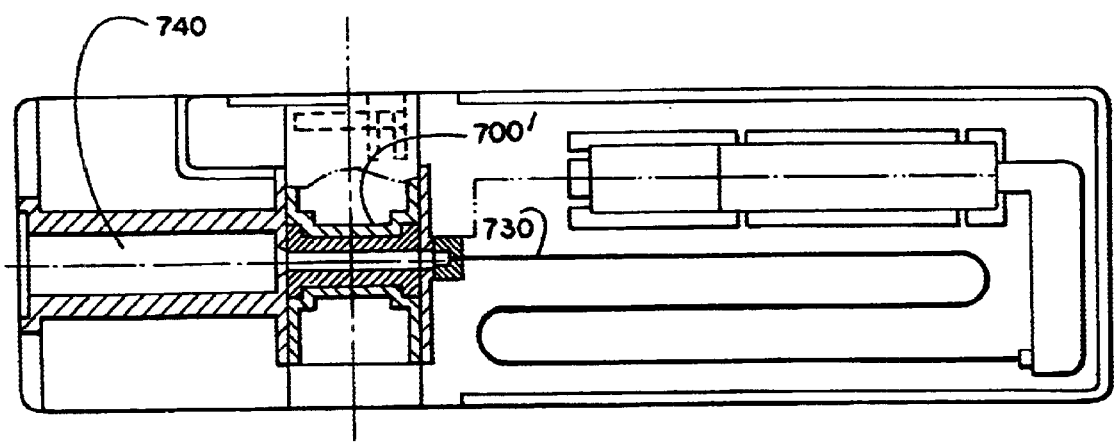
Fig_6

INTEGRATED ASSAY DEVICE AND METHODS OF PRODUCTION AND USE

CROSS-REFERENCE TO RELATED APPLICATION

This application claims priority to pending prior Provisional Application Serial No. 60/077,453, filed on Mar. 10, 1998.

FIELD OF THE INVENTION

This relates to the fields of analytical chemistry and immunology and more specifically relates to an integrated assay device for determining the presence or amount of an analyte in a sample.

BACKGROUND OF THE INVENTION

Assay technology involves methods or instrumentation for the detection or quantitation of one or more antigens or analytes in a sample. Immunoassays are based on the highly specific binding reaction between an antibody, or analyte receptor, and an antigen recognized by the antibody or antigen receptor. Antibodies are binding proteins produced by the immune system of vertebrates in response to substances identified by the immune system as foreign. Immunoassays are commonly used by the medical community to determine the presence, amount or identity of analyte in a biological sample for purposes such as diagnosis and for monitoring therapy. Immunoassays are also used for the detection of environmental contaminants. More recently, immunoassays have been used by non-technical persons in the home for private determinations of medical conditions such as pregnancy and ovulation.

Various approaches for performing homogeneous or heterogeneous immunoassays in both competitive and noncompetitive formats have been described in the literature. Homogeneous immunoassays are performed by combining labeled reagent with a sample and detecting labeled analyte without a separation step. Although homogeneous immunoassays are easy to perform, they are subject to matrix interference. In homogeneous assays it is difficult to ascertain the proportion of bound and free label in the reaction mixture, and thus sophisticated instrumentation is often required to detect and analyze the results. Heterogeneous immunoassay methods contain a separation step in which bound label is separated from free label.

The original enzyme linked immunosorbent assay (ELISA) methods were "competitive" heterogeneous assays in which an enzyme-labeled antigen or antibody competed with an antigen or antibody to be detected for a reaction site on a bead, pad or surface to which one member of an immunologically-coupling pair was attached. Subsequently, the "sandwich" assay, a non-competitive assay, was developed. Non-competitive assays generally utilize antibodies in substantial excess over the concentration of analyte to be determined in the assay. In the sandwich assay, the antibody or antigen to be determined is "sandwiched" by an immunochemical reaction between a solid surface treated with an immunological species reactive with the species to be determined and the same or a different reactive immunological species which had been coupled to a signal-generating label.

Competitive assays generally include a sample suspected of containing analyte, an analyte analog-assay conjugate, and the competition between these components for a limited number of binding sites on the antibody. Due to competition between unbound analyte and analyte analog-assay conjugate for analyte-receptor binding sites, as the analyte concentration increases, the amount of unbound analyte analog-enzyme conjugate increases, thereby decreasing the observed signal associated with the solid phase. The product of the enzyme reaction may then be measured using an instrument such as a spectrophotometer.

Exemplary analytes detected by immunoassays include haptens, hormones, peptides, proteins, deoxyribonucleic acid (DNA), ribonucleic acids (RNA), metabolites of these materials and other substances of either natural or synthetic origin, which may be of diagnostic interest. Binding assays are generally useful for the in vitro determination of the presence and concentration of analyte in body fluids, food products, animal fluids, and environmental samples, such as the determination of specific hormones, peptides, proteins, therapeutic drugs, forensics, paternity and toxic drugs in human or animal blood or urine.

Numerous detection systems have been developed to detect or measure antibody-analyte complexes including enzyme-catalyzed chromogenic reactions, radionuclides, chemiluminescence, bioluminescence, fluorescence, fluorescence polarization and a variety of potentiometric and optical biosensor techniques.

One disadvantage to the presently available immunoassay methods is that multiple manipulations are often required by the individual performing the assay as reagents are added, mixed, incubated, separated and detected, thereby introducing the potential for error. Another disadvantage is that conventional immunoassays require a substantial amount of sample, which could be unavailable, difficult or painful to obtain. In addition, the accuracy of many immunoassays depends on precise sample and reagent measurements and the standardization of conditions such as incubation time and temperature.

Although some simplified immunoassays are available for use by non-technical personnel, these assays lack precision and provide the user with only a "positive" or "negative" response, no quantifiable results are produced. Furthermore, these presently available devices are composed entirely of membranes or absorbent fibrous materials that vary from lot to lot and contain imprecise volumes of sample and the reagents employed.

There is a continuing need for simple, rapid assays for the qualitative, semi-quantitative, and quantitative determination of analytes in a sample. In many situations, such assays need to be simple enough to be performed and interpreted by non-technical users outside of a laboratory.

Thus, simple assay methods are needed that will provide reliable, accurate and rapid results within and outside of conventional laboratory facilities in places such as hospitals, medical offices, homes, on the streets and in the field. There is also a great need for simple, inexpensive and easy-to-use assay devices, particularly immunoassay devices, that are easily manufactured and can be used by technical and non-technical personnel, such as emergency medical technicians, police, firefighters, corrections facilities, and military personnel.

SUMMARY OF THE INVENTION

Assay devices for the detection of analyte in a sample and methods for performing an assay using the devices are provided herein. Also provided are methods of manufacturing the assay devices. The devices can be used for nucleic acid-based assays, chemical assays, and immunoassays, including heterogeneous immunoassays for both competitive and sandwich immunoassay formats. Also provided are simple immunochromatographic strip detection membrane formats having increased precision and accuracy over existing formats.

The device includes self-contained, integrated components for conducting an assay for analyte with minimal manipulation by the individual performing the assay. Upon adding the sample to be analyzed and introducing a force to initiate the assay, no further interaction is required for assay completion. Therefore, by using the device, the assay can be performed by technical and non-technical personnel within and outside of a conventional laboratory environment. The components are miniaturized and compacted into a conveniently-sized, self-contained housing, thereby utilizing a minimal amount of space to facilitate transport and use.

The device is a continuous liquid flow channel having a proximal and a distal end, wherein the sample is introduced to the channel via a sample delivery means so that the sample travels toward the distal end of the channel to a detection membrane in fluid communication with the distal end of the channel. Continuous with the liquid flow channel, are a sample delivery means, one or more reservoirs containing one or more buffers and reagents necessary for conducting the assay, and, optionally, mixing or incubation reservoirs for combining the sample and reagents. The locations of the sample valve and reservoirs, and liquid volume capacities of the flow channel, sample delivery means and reservoirs can be modified and rearranged as needed to optimize the conditions for a wide variety of assay formats and analytes to be detected.

One or more liquid flow channels may be contained within a single housing for simultaneous or consecutive sample analysis.

The assay device optionally includes an initiating means, such as a pump, at the proximal end of the flow channel for initiating the flow of liquid through the liquid flow channel of the device. Reagents, including one or more labeled reagents, are contained within the liquid flow channel either in a liquid or lyophilized state.

The dimensions and geometric shape of the liquid flow channel, including the reagent reservoirs and mixing chambers, regulates the flow rate of the liquids through the channel, thereby controlling incubation, mixing or reaction time. The preferred internal, cross-sectional geometric shape of the liquid flow channel preferably contains at least one angle and is composed of one or more flat surfaces joined at one or more angles, such as a teardrop, pie-shape, triangle, trapezoid, square, rhombus, pentagon, hexagon, etc., rather than merely a continuous internal curved surface such as a circle or oval. Combinations of flat and curved surfaces are also contemplated in the assay device.

The device further includes sample delivery means for introducing a precise, predetermined volume of sample into the liquid flow channel. The sample delivery means optionally contains filtration means for separating interfering substances, such as the cellular components of the sample, before the sample is introduced into the flow of the liquid flow channel.

Buffer is useful for diluting out matrix effects, diluting samples to be within concentration range of detection means, and providing hydrostatic pressure to drive fluid flow. An assay buffer reservoir, located upstream from the location in the liquid flow channel where the sample is introduced by the sample delivery means, is useful for rinsing all of the sample out of the sample delivery means, thereby ensuring that the volume of sample introduced is precisely the predetermined volume.

As an additional option, the device further includes means for separating mobile reagents from immobilized reagents bound to a solid phase substance, such as a solid phase particle.

The detection membrane of the preferred device is a substrate upon which is immobilized means for detecting the labeled reagent that has reacted either directly or indirectly with analyte in the sample. Detection of label can be visual or with the aid of a detector known in the art for the detection of signal produced in an assay reaction, such as a spectrophotometer or reflectometer. The amount of label detected reflects the amount of analyte in the sample being analyzed. Additional reagents are optionally included to calibrate the device or monitor device performance or assay progress, including completion.

The assay method utilizing the device is useful for the detection of a wide variety of analytes including, but not limited to, environmental contaminant analytes, agricultural products, industrial chemicals, water treatment polymers, pharmaceutical drugs, drugs of abuse, and biological analytes, such as antigenic determinants of proteins, polysaccharides, glycoproteins, lipoproteins, nucleic acids and hormones, of organisms such as viruses, bacteria, fungi, parasites, plants and animals, including humans. The assay method is chemical in nature, and the preferred assay method is an immunoassay.

The device is manufactured by adding precise volumes of liquid reagents to predetermined regions of the liquid flow channel either prior to encapsulation of the channel or through apertures from the exterior of the housing to the channel that are subsequently sealed. The reagents may be lyophilized, or otherwise dried, to preserve activity or facilitate immobilization during transportation or storage.

It is therefore an object of the present invention to provide an assay device for immunoassays, nucleic acid-based assays and chemical assays that is self-contained and automatically executes all the steps of a multi-step assay through the use of precise control of the geometry of microfluidic channels and chambers etched or molded in the assay device housing material.

It is a further object of the present invention to provide an integrated means for delivering a precise, predetermined volume of sample to an assay device.

It is a further object of the present invention to provide an integrated means for preparing or processing a sample upon introduction of the sample to an assay device such as by filtration or extraction, thereby eliminating the need to process the sample.

It is a further object of the present invention to provide an assay device and method for the detection of analyte in a sample that can be used to detect a wide variety of analytes.

It is a further object of the present invention to provide an assay device and method for the detection of analyte in a sample that is simple, inexpensive, portable and user-friendly and can be utilized successfully by non-scientific personnel.

It is a further object of the present invention to provide an assay device and method for the detection of analyte in a sample that provides reliable, reproducible results on-site, in the home, or in the field.

It is a further object of the present invention to provide an assay device and method for the unattended detection of analyte after introduction of sample to the device.

It is a further object of the present invention to provide an assay device and method for the detection of analyte in a sample that requires no critical timing events or mixing of reagents by the individual performing the assay because all incubation times are determined by the dimensions of the device, such as the capillary channel geometry.

It is a further object of the present invention to provide an assay device and method for the detection of analyte in a sample without requiring precise sample or reagent measurements by the individual performing the assay.

It is a further object of the present invention to provide an assay device and method for the detection of analyte in a sample that provides results that are very accurate, very reproducible and highly controlled.

It is a further object of the present invention to provide an assay device and method for the detection of analyte in a sample that produces rapid results.

It is a further object of the present invention to provide a flexible assay device and method that can be adapted to various samples, assay formats and detection parameters.

It is a further object of the present invention to provide an assay device and method for the detection of analyte in a sample that produces results that can be analyzed by the naked eye in the absence of, or with minimal, instrumentation or training of the individual performing the assay.

It is a further object of the present invention to provide an assay device and method that is easily and inexpensively manufactured.

It is a further object of the present invention to provide assay and immunochromatographic strip detection membrane formats that provide for precise and accurate detection of analyte in a sample.

These and other objects of the present invention will become apparent after reading the following detailed description of the disclosed embodiments and the appended claims.

BRIEF DESCRIPTION OF THE DRAWINGS

FIG. 1 is a schematic representation of a first preferred embodiment of an immunoassay device, as described herein, in which a solid phase bead is separated from a mobile phase containing non-reacted reagents by a separating membrane.

FIG. 2 is a schematic representation of a second preferred embodiment of an immunoassay device, as described herein, in which cellular components of a sample are retained on a membrane prior to introduction of the sample to the fluid flow channel.

FIG. 3 is a schematic representation of a third preferred embodiment of an immunoassay device, as described herein, utilizing an air pump, sample separation membrane, and mixing chambers.

FIG. 4 is a schematic representation of a fourth preferred embodiment of an immunoassay device, as described herein, wherein the assay is driven by capillary action.

FIG. 5 is a side view of an immunoassay device, as described herein, showing the sample delivery valve in the sample loading mode.

FIG. 6 is a top view of an immunoassay device, as described herein, in a housing that is cut away to show the sample delivery valve in the assay analysis mode with the capillary channel aligned with the liquid flow channel.

DETAILED DESCRIPTION OF THE DESCLOSED EMBODIMENTS

An assay device and method for the detection of analyte in a sample and methods for manufacturing the assay device are described herein. The device is useful for immunoassays, including heterogeneous assays for both competitive and sandwich immunoassay formats; nucleic acid-based assays; and chemical assays. Also provided are immunoassay methods, or formats, for simple, accurate and precise determination of analyte in a sample.

The device includes self-contained, integrated components for conducting a "point of service" or "point of care" immunoassay for analyte with minimal manipulation by the individual performing the immunoassay. Upon adding the sample to be analyzed and applying a physical force to initiate the assay, which may be accomplished as the sample is delivered to the device, no further interaction or instrumentation is required for assay completion. The device itself provides for sequential and multiple assay steps without user attention. Therefore, by using the device, the assay can be performed by technical and non-technical personnel within and outside of a conventional laboratory environment. The components are miniaturized, inexpensive, and compacted into a conveniently-sized, self-contained housing, thereby utilizing a minimal amount of space to facilitate transport and use.

The device is a continuous liquid flow channel having a proximal and a distal end. When introduced into the flow channel, as described in more detail below, a sample travels with liquid, such as a buffer, contained in or introduced into the flow channel, toward the distal end of the flow channel. At the distal end of the flow channel the sample encounters a detection membrane The detection membrane is in fluid communication with the distal end of the flow channel.

Continuous with the liquid flow channel, are a sample delivery means, one or more reservoirs containing the reagents necessary for conducting the assay, and, optionally, mixing or incubation reservoirs for combining the sample and reagents. The locations of the sample valve and reservoirs, and liquid volume capacities of the flow channel can be modified or rearranged as needed to optimize the conditions for a wide variety of assay formats and analytes to be detected. When introduced into the flow channel, the sample preferably travels with the other liquids, such as the buffer and reagents, or reconstituted reagents, as a discrete bolus, or bolus slug, of reaction mixture liquid from the proximal end toward the distal end of the flow channel. One or more liquid flow channels and detection membranes may be contained within a single housing for simultaneous or consecutive sample analysis.

The liquid flow channel is preferably composed of a first channel segment, upstream from the sample delivery means, and a second channel segment, downstream from the sample delivery means. The first segment and second segment are optimally joined to form a continuous liquid flow channel when the sample delivery means is adjusted to align a capillary channel within the sample delivery means with the first and second liquid flow channel segments so that the segments are both in fluid communication with the capillary channel of the valve.

The assay device includes an initiating means for initiating the flow of liquid through the liquid flow channel of the device from the proximal to distal end. Preferably, the introduction of sample into the liquid flow channel is sufficient to initiate the flow of liquid through the channel by capillary action and maintain the flow of liquid until it reaches the distal end of the detection membrane or end-of-test indicator, described in more detail below. Alternatively, an optional flow initiator, such as a pump, may be employed at the proximal end of the channel. Preferably, after initiation of liquid flow, an assay buffer, contained within an assay reservoir or within a portion of the liquid flow channel, travels as a bolus of liquid contacting the reagents and sample in a sequential fashion as the liquid flows in a longitudinal direction within the liquid flow channel from the proximal to distal end. Buffer is useful for diluting out matrix effects, diluting samples to be within concentration range of detection means, and providing hydrostatic pressure to drive fluid flow.

Reagents, including one or more labeled reagents, are contained within the liquid flow channel either in a liquid or lyophilized state. As the bolus of liquid passes over the lyophilized reagents, the reagents are solubilized or suspended in the liquid and are capable of reacting with the other components in the liquid. The geometry of the liquid flow channel regulates the flow rate of the liquids through the channel, thereby controlling incubation, mixing or reaction time. The internal dimensions, particularly the cross-sectional area, are preferably small enough to result in capillary action. For example, the internal cross-sectional area of the liquid flow channel may be tapered from the proximal to the distal end to enhance capillary action. The preferred cross-sectional geometric shape may be of any size, shape or form, including circles and ovals, provided that it is sufficient to promote capillary action. The preferred cross-sectional geometric shape of the internal surface of the liquid flow channel contains at least one angle and is composed of one or more flat surfaces joined at one or more angles, such as a teardrop, pie-shape, triangle, trapezoid, square, rhombus, pentagon, hexagon, etc., rather than a continuous internal curved surface such as a circle or oval. Combinations of flat and curved internal surfaces are also contemplated in the immunoassay device.

The device further includes a sample delivery means containing a capillary channel for introducing a precise volume of sample into the liquid flow channel. The preferred sample delivery means is a valve or slide mechanisms that is rotated or slid to align the capillary channel of the sample delivery means with the liquid flow channel. Most preferably, the sample delivery means is a rotatable sample delivery means. The sample delivery means ensures the reproducibility of the volume of sample analyzed by the device. Therefore, the sample volume need not be measured prior to being applied to the sample delivery means and is not subject to human error as long as the volume is in excess of the predetermined volume measured by the sample delivery means.

The sample delivery means optionally contains a filter for removing interfering substances, such as cellular components or particulate matter in the sample, before the sample is introduced into the flow of the liquid flow channel. The sample delivery means may also contain an extraction means for separating organic molecules in a sample from one another. For example, the filter may provide a solid phase extraction step or an affinity purification technique.

As an additional option, the device further includes a compartment or chamber for separating mobile reagents from immobilized reagents bound to a solid phase substance, such as a solid phase bead.

The detection membrane of the preferred device is a detection membrane upon which is immobilized the appropriate reagents for detecting the labeled reagent that has reacted either directly or indirectly with analyte in the sample. Detection of label can be visual or with the aid of a detector known in the art for the detection of signal produced in an immunoassay reaction, such as a spectrophotometer, reflectometer, fluorometer and the like. The amount of label detected reflects the amount of analyte in the sample being analyzed. Additional reagents are optionally included to calibrate the device, act as a control, or monitor device performance or assay progress, including completion of the assay.

In accordance with the preferred assay method, a sample is applied or added to a sample well that is in fluid communication with the sample delivery means. The sample delivery means is manipulated to deliver the sample to the liquid flow channel. For example, if the sample delivery means is a valve that is rotatably mounted within the liquid flow channel, the sample is introduced into the flow of the liquid flow channel by rotating the valve. When the valve is in alignment with the flow of the fluid flow channel, assay test buffer, which may be maintained in a buffer reservoir upstream from the sample valve when the valve is in the closed position, is released from the buffer reservoir and is drawn through the liquid flow channel by capillary action, thereby rinsing the capillary tube containing the sample. Alternatively, the buffer is carried through the fluid flow channel by positive or negative pressure or gravity. The sample is then carried with the fluid flow of the buffer along the path of the flow channel toward the distal end of the immunoassay device. As the fluid flows through the fluid flow channel, the reagents that have been preapplied to the fluid flow channel are reconstituted and mixed with sample flowing through the channel and react with analyte in the sample to form a reaction mixture. Labeled reagents are then detected on a chromatographic test strip. The detection and amount of label are related to the presence and concentration of analyte in the sample.

The assay method utilizing the device is useful for the detection of a wide variety of analytes including, but not limited to, environmental contaminant analytes, agricultural products, industrial chemicals, water treatment polymers, pharmaceutical drugs, drugs of abuse, and biological analytes, such as antigenic determinants of proteins, polysaccharides, glycoproteins, lipoproteins, nucleic acids and hormones, of organisms such as viruses, bacteria, fungi, parasites, plants and animals, including humans.

The device is manufactured by encapsulating a liquid flow channel in a housing; adding precise volumes of liquid reagents to predetermined regions of the liquid flow channel either prior to encapsulation of the channel or through apertures from the exterior of the housing to the channel that are subsequently sealed. The reagents may be lyophilized to preserve activity or facilitate immobilization during transportation or storage.

Assay Method and Device Features

A limitation to existing immunochromatographic or lateral flow tests is that all of the test components are incorporated onto the test strip. The sample analyte is applied to the strip test and comes into contact with reagents that are either mobilized or immobilized in zones along the length of the strip. The extent to which reaction components mix, incubate, and bind to various reagents and zones is dependent on the fluid flow rate through the fibrous materials, such as membranes, filters, and pads. Such materials are know to be heterogenous in their composition. Therefore, tests made with such materials demonstrate variable results.

In addition, in order to minimize variability and improve precision, it is preferable to allow the reactants of a test to reach chemical equilibrium. A limitation of existing immunochromatographic or lateral flow strip tests is that the immunochemical reactions occur on the test strip as the reactants pass through the various zones of the test. During the short period of time that the various reactants are in contact with the zones on the test strip, insufficient time elapses to allow the reactants to reach chemical equilibrium. The heterogeneous nature of strip test components such as membranes, filters, pads and the like, results in variability in the rate of fluid flow through these components and the various reaction zones incorporated therein. Thus, the short (non-equilibrium) and variable amount of time in which the reactants are in contact with each other in presently available immunochromatographic or lateral flow devices results in unacceptable variability in many critical test applications.

The assay device described herein provides for mixing, incubating and reacting the critical test components outside of the membrane detection strip in a manner that overcomes the limitations of existing immunochromatographic or lateral flow strip tests. The precise dimensions and geometries of the fluid channel more precisely control flow rate and provide for mixing and incubation conditions that allow the critical chemical or immunochemical reactions to substantially reach equilibrium. The membrane detection strip of the device described herein serves to capture the products of a substantially completed chemical or immunochemical test, which have been produced prior to the arrival of the reaction mixture at the detection membrane.

The immunoassay methods or formats described herein, which can be conducted with or without the assay device, are simple to use, but are more precise, reliable, robust and accurate than existing methods. The assay device provides a highly effective means for executing such immunoassay methods.

Definitions

The terms "a", "an" and "the" as used herein are defined to mean "one or more" and include the plural unless the context is inappropriate.

The term "analyte" refers to a drug, hormone, chemical, toxin, compound, receptor, nucleic acid molecule or other molecule and fragments thereof to be measured by the device and method described herein.

The term "binding molecule" is defined herein to include an antibody; antibody fragment that binds to analyte or ligand; antibody epitope that binds to analyte or ligand; Fab fragment; monoclonal antibody; polyclonal antibody; antibody conjugate such as an antibody conjugated to a nucleic acid molecule; antibody conjugated to a hapten or other ligand; receptor; receptor fragment capable of binding to analyte or ligand; or nucleic acid molecule, including RNA, DNA and cDNA.

Housing

The integrated assay device contains various components for buffer storage, sample processing and measurement, fluid flow initiation and maintenance, sample introduction, reagent storage, reagent mixing and analyte detection, all contained within a housing that holds and protects the components from contamination or interference from the environment. The housing is preferably composed of an inert material and may optionally be transparent or translucent, or contain transparent regions or windows, to permit visual monitoring of the progress of the sample within the sample valve and along the length of the fluid channel to the end-of-test indicator. Preferably, the housing is composed of an inert material that will not react with any of the components of the reaction mixture, such as plastic, particularly polystyrene; ceramic; metal; glass; nylon; polyvinylidene difluoride; cellulose acetate; silicon; or a similar material.

The housing is preferably preshaped in two or more sections to fit around and securely contain all of the components of the device when the sections are joined together. The housing is shaped to facilitate the addition of reagents, assembly and manufacturing. The sections are joined using physical means, such as bolts, screws or a friction-based fitting, or chemical bonding in which an adhesive, heat, or sonication is applied to fuse the sections. Alternatively, the housing is extruded or molded around the components while in a liquid or semi-solid, pliable state that hardens with time to form an inflexible, solid barrier.

The preferred size of the housing is one that fits within the palm of the hand of the individual conducting the assay. It will be understood by those skilled in the art that the size of the housing may be larger or smaller depending on the size of the components and the complexity of the assay.

Optionally, the housing includes or is composed of an insulating or temperature controlled material that maintains a stable environment while the assay device is being utilized. For example, the housing may include a heating or cooling element that can be thermostatically controlled or may contain phase change agents that are able to accept and release heat without changing temperature. Furthermore, the housing may be impermeable to liquids so that the housing protects the components from moisture and permits submersion in a temperature controlled water bath.

The house is optionally designed to fit within the dimensions of an instrument capable of detecting the detectable label on the immunochromatographic strip.

Flow Initiation

A preferred method for initiating the assay method is to stimulate an assay buffer, contained in a buffer reservoir at the proximal end of the flow channel, to exit the buffer reservoir and enter the flow channel. This is generally achieved by applying a positive force at the proximal end of the flow channel, a negative force downstream from the fluid source reservoir, or by utilizing the force of gravity. The force may be applied directly or indirectly to the assay buffer reservoir. The preferred force is a simple physical action.

Most preferably, the flow of the assay buffer from the buffer reservoir to the distal end of the device is initiated and maintained when the sample is delivered to the liquid flow channel, such as by manipulating the sample delivery means to place it in alignment with the liquid flow channel, as described in more detail below, thereby causing the assay buffer to flow from the reservoir by capillary action. In order to maintain the flow of liquid from the proximal to the distal end of the liquid flow channel, the channel should be of sufficiently small dimensions to maintain capillary flow. In addition, the internal, cross-sectional shape of the channel is optimally composed of flat surfaces joined at one or more angles, rather than curved surfaces. This shape promotes and maintains fluid flow through the device because the capillarity at sharp angles is greater than the capillarity at flat surfaces. Exemplary channel shapes contain three or more sides, at least one of which is a flat surface. Most preferably, the internal shape of the liquid flow channel is a trapezoid shape.

Alternatively, a pump or vacuum is used to physically move the liquid contained in the reservoir into the liquid channel. Preferably, the pump is a manual air pump that is activated by the application of pressure, such as pressure applied between the index finger and thumb of the hand of the individual performing the assay. Alternatively, the pump is activated by electrical or mechanical means. The pump may be external to the housing so that it is easily accessible to the application of force, as shown in FIG. 1. Negative or positive pressure may alternatively be applied by means of a plunger device, such as a syringe containing air or a liquid, which is attached to an entrance port in the assay device.

Alternatively, the assay buffer reservoir is composed of a flexible material, such as a flexible plastic, and the contents of the assay buffer reservoir are expelled into the fluid channel by the application of physical force directly to the reservoir, as shown in FIG. 2.

Assay Buffer

The assay buffer is a fluid that moves through the liquid flow channel from the proximal end of the assay device to the distal end. The assay buffer dissolves, carries or moves the sample and reagents along the liquid flow channel, through the various channels, reservoirs and mixing chambers, onto the detection membrane, and to the end of test indicator, if present.

The assay buffer may be contained in a buffer reservoir and is released from the reservoir when the sample is delivered to the liquid flow channel. If the sample delivery means is a valve, the buffer is retained in the reservoir when the valve is in the closed position. When the valve is moved to the "open" position, in which the capillary channel in the valve is aligned with the liquid flow channel, buffer flow is initiated as described above.

The buffer is preferably an aqueous solution capable of mixing with, dissolving, or reconstituting, if in lyophilized form, reagents contained within the liquid flow channel and the sample analyte. More preferably, the fluid is an assay reagent buffer such as phosphate buffered saline (PBS).

The assay buffer may optionally contain one or more reactants of the assay reaction, such as an antibody, antigen or other reagent.

Reagent Reservoir

A reagent used to capture, label, detect, or amplify the analyte, such as a labeled or unlabeled antibody or antigen, is stored in a reservoir within or in liquid flow communication with the liquid flow channel until contacted by the assay buffer as it progresses from the proximal to the distal end of the liquid flow channel. Preferably the reagent is added to a capillary segment of the liquid flow channel during manufacture of the assay device. The reagent is then lyophilized, or otherwise dried, so that it remains in the capillary segment in which it was placed until reconstituted.

Reconstitution occurs as the assay buffer and sample pass through that segment of the channel. The capillary segment of the liquid flow channel in which reagent is stored is referred to herein as a "reagent channel reservoir".

It will be understood that, when more than one reagent is utilized in the assay, the reagents may be stored together in the same reagent reservoir of the liquid flow channel or may be placed in separate reservoirs, especially if interaction between the reagents is undesirable or sequential contact of sample and regents is desirable. The reagent reservoir or reservoirs may be located within the liquid flow channel either before or after the sample delivery means. Most preferably, the device includes at least two reagent reservoirs with a first reservoir that comes into contact with the assay buffer and sample before a second reservoir, so that the reaction mixture contains both the sample and the first reagent. This orientation simulates a conventional immunoassay method in which the sample is reacted with a first reagent, such as an antibody and then the sample-reagent complex is reacted with a second reagent, such as a labeled antibody or antibody that has been conjugated to a solid phase for subsequent detection or separation.

Reagents

Suitable reagents include a first "binding molecule" having immunological specificity for the analyte and a second "binding molecule" having specificity for the first binding molecule or the analyte-binding molecule complex. Exemplary binding molecules include, but are not limited to, an antibody; an antibody fragment that includes an immunoreactive portion of an antibody or epitope for the analyte; an antibody conjugate such as an antibody conjugated to a nucleic acid molecule; an antibody conjugated to a hapten or other ligand; an antibody conjugated to a detectable substance such as an enzyme, colored particle or other label known in the art; a receptor; a receptor fragment capable of binding to a ligand; a complementary nucleic acid sequence; an antigen, including a hapten or analyte analog; a fragment of an antigen; and an antigen conjugate.

Preferably, the binding molecule is an antibody or antibody conjugate which, when reacted with the sample to be tested, is free in solution, thus providing for the most rapid and optimal reaction with analyte. Accordingly, the degree of purity of the antibody has minimal effect on the assay. Purified antibody, partially purified antibody, whole serum and ascites containing the antibody are appropriate provided that the antibody exhibits an affinity for analyte. The antibody may be monoclonal or polyclonal. A monoclonal antibody is particularly useful in situations where a high degree of specificity is desired.

Methods for preparing polyclonal and monoclonal antibodies are well known to those skilled in the art. The preferred method for preparing monoclonal antibodies is a modified version of the method of Kearney, et al., *J. Immunol.* 123:1548–1558 (1979), which is incorporated by reference herein. Briefly, animals such as mice or rabbits are inoculated with the immunogen in adjuvant, and spleen cells are harvested and mixed with a myeloma cell line. The cells are induced to fuse by the addition of polyethylene glycol. Hybridomas are chemically selected by plating the cells in a selection medium containing hypoxanthine, aminopterin and thymidine (HAT). Hybridomas are subsequently screened for the ability to produce monoclonal antibodies having the desired sensitivity and specificity. Hybridomas producing antibodies are cloned, expanded and stored frozen for future production.

The binding molecule may be labeled directly with a detectable label. Labels for use in immunoassays are generally known to those skilled in the art and include enzymes, radioisotopes, and fluorescent, luminescent and chromogenic substances including colored particles such as colloidal gold and latex beads. Alternatively, the antibody is labeled indirectly by reaction with a labeled substance having an affinity for immunoglobulin, such as protein A or G or second antibodies. The antibody may be conjugated with a second substance and detected with a labeled third substance having an affinity for the second substance conjugated to the antibody. For example, the antibody may be conjugated to biotin and the antibody-biotin conjugate detected using labeled avidin or streptavidin. Similarly, the antibody may be conjugated to a hapten and the antibody-hapten conjugate detected using labeled anti-hapten antibody. These and other methods of labeling antibodies and assay conjugates are well known to those skilled in the art.

Binding molecules, such as antibodies, specific for a multitude of analytes are readily available from commercial sources, hybridoma depositories (such as the American Type Culture Collection, Rockville, Md.), and research laboratories. Alternatively, the binding molecule is an antibody conjugate. For example, the binding molecule is an antibody to which has been conjugated, or otherwise attached, a nucleic acid molecule.

Suitable reagents also include particles or beads to which have been conjugated or coated a binding molecule or analyte. For example, an analyte-coated particle would be used for a competitive immunoassay. The term "coated particle" is defined herein as a particle to which is attached to the outer surface one or more molecules. The particle need not be completely covered or continuously coated with the molecules. The particle may be colored so that its progress through the liquid flow channel can be visually monitored.

Preferably, the particle is a naturally occurring or synthetic substance, irregularly or regularly shaped (such as a sphere, bead or the like) to which an analyte or binding molecule is capable of being attached, either directly or indirectly. The particle may be solid, hollow or semi-solid and is preferably water-insoluble. Exemplary particles found in nature include liposomes, spores, pollen, cells, and microorganisms such as plankton, bacteria, or fungi. Synthetic particles may be formed from organic or inorganic materials, many of which are commercially available from companies such as Polysciences, Inc. (Warrington, Pa.). Preferred particles include, but are not limited to, chromatography media such as those commercially available from Pharmacia Biotech Inc. (Piscataway, N.J.) and Supelco, Inc. (Bellefonte, Pa.). Most preferably, the coated particle is a latex bead.

The analyte or binding molecule may be directly or indirectly attached to the particle in accordance with methods known to those skilled in the art. For direct attachment, the analyte or binding molecule is adsorbed or covalently bonded to the surface of the particle such as by reaction with functional groups on the particle such as amino, carboxyl, sulfhydryl, aldehyde, hydrazide, epoxide, chloromethyl, hydroxyl, and other groups known in the art. For indirect attachment, the analyte or binding molecule is conjugated to a reactive molecule, such as a protein, polymer or other molecule, that is then adsorbed or conjugated to the surface of the particle. Alternatively, the particle is first coated with a reactive material that facilitates coupling of the analyte or binding molecule. A suitable reactive material is an immunochemically unreactive molecule, such as a protein or polysaccharide, to which the analyte or binding molecule is readily attached. It will be understood by those skilled in the art that the coated particle may be blocked with a suitable material such as a detergent, protein or polymer, to prevent non-specific binding thereto. It will be further understood that the terms "coating" and "coated" define a particle to which is attached to its outer surface one or more molecules. The particle need not be completely covered or continuously coated with the molecules.

Sample Delivery Means

The sample delivery means is capable of delivering a precise amount of sample to the liquid flow channel without the need to premeasure the volume of sample being delivered. The sample delivery means includes a sample well, into which the sample is placed, and means for delivering the contents of the sample well into the flow path of the liquid flow channel. Preferably, the contents of the sample well flow into a sample tube having a calibrated volume, which is contained within the valve. The preferred sample tube is a capillary tube. It will be understood by those skilled in the art that the volume of the sample capillary tube may be manually adjustable to accommodate a variety of sample sizes. The sample delivery means is preferably a valve containing the sample capillary tube. The sample delivery means is connected to the liquid flow channel so that the capillary tube can be easily placed into the path of the liquid flow channel by a simple manual motion, such as rotation or a sliding action. Exemplary valves include Luer Lock™ valves or similar disk-shaped valves having an aperture bored across the diameter of the valve.

As shown in FIG. 5, the preferred sample delivery means is configured in such a way that the capillary tube 700 is aligned with an aperture 710 in the sample well 720 when sample is being added to the sample well. The sample then fills the capillary tube 700. When full of sample, the capillary tube contains a predetermined volume of sample. The preferred volume of the sample capillary ranges from 0.1 to 100 $\mu$L. A 10 $\mu$L volume is most preferred. Any sample in excess of the volume of the capillary tube remains in the sample well. Subsequently, as shown in FIG. 6, the valve is rotated to align the capillary tube 700' within the liquid flow channel 730 so that the fluid source, such as a buffer, flows from the buffer reservoir 740 through the sample capillary tube 700', and the combination of buffer and sample proceeds toward the distal end of the liquid flow channel 730. It will be understood by those skilled in the art that the flow may be a bolus slug of liquid sample, buffer and reagents followed by air, such as when the flow is initiated by gravity or a negative or positive pressure or capillary action.

Optionally, as shown in FIGS. 2 and 3, the sample delivery means contains a sample separating membrane between the sample well and the sample capillary tube for retaining the cellular or particulate components of the sample, thereby preventing delivery of these components into the liquid flow channel. The membrane, or filter, is preferably an inert, porous material having a pore size diameter or mesh of sufficient dimension to exclude passage of large sample components, such as cells, while allowing passage of soluble components. For example, if the sample is whole blood, the membrane retains blood cells, such as erythrocytes and lymphocytes, but allows blood plasma containing smaller molecules, such as viruses, bacteria, drugs, and cytokines to pass through into the sample capillary tube for analysis. The filter media may be composed of natural fiber, glass fiber, synthetic fiber or a fiber blend, particularly a glass-synthetic blend. These materials may be amended with various additives such as surfactants, polymers and/or proteins to aid in the filtration process. These materials are commercially available.

The optimal pore size of the sample separating membrane is dependent on the biological or chemical composition of the sample and the size of the particulate matter to be filtered out. For example, the pore size of the preferred membrane for a blood sample has a diameter between approximately 0.1 and 25 $\mu$m. A membrane having a pore size diameter of approximately 5 $\mu$m is most preferred for filtering out erythrocytes. The membrane is composed of an inert material that will not react with the analyte, such as plastic, ceramic, metal, glass fibers, nylon, paper, nitrocellulose, polytetrafluoroethylene, polypropylene, polyvinylidene difluoride, cellulose acetate or a similar material. The preferred material is nylon, nitrocellulose, or similar materials known to those skilled in the art. The membrane has a minimum thickness that will withstand the conditions under which it will be employed without ripping or tearing and a maximum thickness that will allow for the rapid passage of the soluble components of the reaction mixture. Membranes having these desired characteristics are commercially available from laboratory product suppliers such as Millipore, Corp. (Bedford, Mass.) or Schleicher & Schuell, Inc. (Keene, N.H.).

The sample membrane may optionally provide solid phase extraction of the sample to separate or remove one or more components from the sample using the well known chromatographic principles of normal phase, reverse phase and ion exchange chromatography. Such membranes are commercially available from laboratory supply companies such as Millipore (Milford, Mass.) and Alltech (Deerfield, Ill.). In addition, the sample membrane may optionally provide for extraction of specific components of the sample by means of specific affinity ligands, such as antibodies, antigens, receptors, nucleic acids and other substances using the well known principles of affinity chromatography.

Alternatively, the sample delivery means is an aperture in the liquid flow chamber into which the needle or a connection fitting of a syringe containing the sample is inserted and the syringe plunger depressed to provide sample delivery.

Optionally, as shown in FIGS. 2 and 3, the sample delivery means includes an absorbent material, such as blotting paper, in longitudinal alignment with the capillary tube at the end of the capillary tube opposite to the end aligned with the aperture in the sample well. The absorbent material acts as a sample sink to enhance the flow of sample from the sample well into the sample capillary tube. The sample sink may contain an indicator, or dye, that travels with the liquid sample to indicate that the sample capillary tube has been properly filled with sample, thereby ensuring delivery of a precise sample volume. Movement of the dye through the absorbent material to a predetermined location, such as an observation window in the assay device housing is visually detectable.

Mixing Chamber

While it is known that diffusional mixing within capillary channels exhibiting laminar flow is high, it is contemplated that the narrow dimensions of the capillary segments of the liquid flow channel may not permit adequate interaction between the various fluids being carried along the liquid flow channel. Therefore, the capillary geometry may optionally be adjusted to include structural features to promote turbulent flow and mixing.

Alternatively, when an applied force is used to maintain fluid flow through the liquid flow channel, one or more mixing, or incubation, chambers are optionally included in the liquid flow channel to provide a space having sufficient volume capacity to allow the reagents and sample to mix and react. The mixing chambers are integrated segments of the liquid flow channel having dimensions larger than the dimensions of the capillary segments of the liquid flow channel. Preferably, the maximum volume of each mixing chamber is less than the volume of the assay buffer reservoir so that the entire contents of the reaction volume are pooled together and uniformly mixed. The mixing chamber may include means for physically mixing the contents of the chamber, such as magnetic particles, that rotate when the assay device is placed on a rotating magnet, or structural features such as posts or walls having irregular shapes or insoluble particles, all or any of which promote turbulent flow and mixing.

Reagent Separation Means

Assays contemplated herein include the use of solid phase beads or particles to which have been attached a binding molecule that binds to unreacted reagents, thereby reducing false positive results and facilitating detection of analyte. These particles may be included as reagents in a reagent reservoir as described above. Suitable particles are mobile latex beads, preferably dried, having coated on their surfaces one member of a binding pair. The particles are preferably contained in a lyophilized state within a reservoir of the liquid flow channel. The particles are reconstituted when contacted with a liquid, such as buffer or sample, as it travels toward the distal end of the liquid flow channel. The particles preferably react with and bind to either analyte or a binding molecule, such as an antibody.

The particles may be removed or separated from the reaction mixture before or as the reaction mixture enters the detection membrane at the distal end of the liquid fluid channel. Separation is achieved by including a porous membrane in the liquid flow channel downstream of the reagent reservoir containing the particles and upstream to the detection membrane. The pores in the porous membrane are large enough to allow penetration of the fluid component of the reaction mixture, containing fluids and small molecules, but not the particles, which are excluded from entering the pores and are retained on the upstream surface of the porous membrane. Alternatively, the particles may be removed, and separation effected directly, by the detection membrane.

The separation membrane is preferably an inert, porous material composed of materials having the characteristics of the sample separating membrane described above.

An alternative means for effecting a separation step in the device described herein includes the use of solid phase magnetic particles to which reagents have been attached. The particles react with sample or other reagents and are subsequently trapped at a point downstream by a magnet, either imbedded in the device housing or external to the device.

Detection Membrane

The detection membrane is an immunochromatographic membrane or strip, having reagents deposited in zones along the longitudinal length of the membrane. The reagents on the membrane provide means for detecting the reaction products of an immunochemical reaction which has been essentially completed prior to interaction with the detection membrane, preferably by visually detecting a labeled substance or substances, such as colloidal gold, that have been bound to reagents that bind to the products of the immunochemical reaction. Alternatively, the reagents may detect the absence of labeled substance, and the label may be detected using instrumentation known to those skilled in the art such as a spectrophotometer, reflectometer or fluorescence detector. The reagents on the membrane may be immobilized or may be diffusable but contained on the membrane in a solid or semisolid state that, when contacted with the fluid source-sample-reagent mixture as it passes through the detection membrane, becomes mobile and moves with the fluid source toward the distal end of the detection membrane. Reagents may also be included on the immunochromatographic strip to enhance or clarify the signal produced by the label being detected. Additional reagents are optionally incorporated in zones on the detection membrane to calibrate the assay device or monitor device performance or assay progress.

The membrane is preferably a non-woven substrate upon which the reagents can be immobilized or deposited, and which is capable of conveying fluid in a fluid flow direction generally parallel to the longitudinal length of the chromatographic strip. Desirable chromatographic strips are composed of a fluid-conducting material including, but not limited to, nylon, polyethylene, glass fiber, nitrocellulose, cellulose, and other common membrane matrices or bibulous materials. The preferred chromatographic strip is composed of nitrocellulose. The membrane of the chromatographic strip is optionally backed with, or laminated to, another material. Desirable backing or laminating material is polyethylene or vinyl, although other suitable materials known in the art may be used.

Immunoassay Format

In a preferred competitive immunoassay format, the critical, non-immobilized immunochemical reagents are contained in reagent reservoirs in the fluid flow channel upstream of the detection membrane so that the membrane contains a minimal number of reagent zones. Preferably, a first reagent reservoir in the liquid flow channel contains a diffusable (or mobile) first binding partner; a second reagent reservoir contains labeled, diffusable analyte that binds to substantially all of the first binding partner in the absence of analyte in the sample to form a labeled analyte-first binding partner complex; and the immunochromatographic detection membrane, or strip, has the following two zones: 1) a detection zone with sufficient immobilized second binding partner to bind substantially all of the first binding partner, and 2) a detection zone with an immobilized binding moiety specific for the labeled analyte or a component of the labeled analyte reagent. The zones should be separated on the strip to enable the individual performing the assay to determine whether a signal occurs in the first or second zone or to compare the intensity of signal in the two zones for a quantitative evaluation. It will be understood by those skilled in the art that the location of the first binding partner and labeled, diffusable analyte within the liquid flow channel can be in any order such that the first binding partner is either upstream or downstream from the labeled, diffusable analyte.

When a sample containing analyte is introduced into the liquid flow channel, the analyte in the sample binds to the first binding partner, thereby preventing the first binding partner from binding to labeled analyte. The first binding partner is then captured by the immobilized second binding partner in the first zone of the detection membrane, allowing the labeled analyte to become bound to the immobilized binding moiety in the second zone of the detection membrane. Detection of signal in the second zone of the detection membrane indicates the presence of analyte in the sample.

In the absence of analyte, the first binding partner from the first reagent reservoir binds to the labeled analyte in the second reagent reservoir. The labeled analyte-first binding partner complex is then bound to the immobilized second binding partner in the first zone of the detection membrane, thereby preventing the migration of label to the second zone of the detection membrane. The presence of signal in the first zone of the detection membrane indicates the absence of analyte in the sample.

It will be understood by those skilled in the art that, in the absence of an integrated assay device as described herein, the immunoassay formats described above and below may be employed using conventional containers or reaction vessels to hold the reagents, either sequentially lyophilized in a single container or stored as liquids in separate vessels, and the proximal end of the immunochromatographic strip is dipped into the vessel after the sample and reactants have reacted, or the reaction mixture is applied to the proximal end of the strip, and the strip is analyzed as described above.

An alternative competitive immunoassay format includes a first reagent reservoir containing a mobile, labeled first binding partner, such as a gold-labeled antibody, specific for the analyte to be detected, and a second reagent reservoir containing a mobile analyte conjugate. In this format, the immunochromatographic detection membrane has two zones containing the following immobilized reagents: 1) a second binding partner specific for any component of the analyte conjugate, and 2) a third binding partner specific for the labeled first binding partner. It will be understood by those skilled in the art that the location of the first binding partner and mobile analyte conjugate within the liquid flow channel can be in any order such that the first binding partner is either upstream or downstream from the mobile analyte conjugate.

In the absence of analyte, the mobile, labeled first binding partner is carried by the sample, as it travels from the proximal to the distal end of the liquid flow channel, to the second reagent reservoir where the labeled first binding partner bind to the analyte conjugate. The reaction mixture then flows to the detection membrane where the labeled first binding partner-analyte conjugate complex is captured in the first detection zone by the second binding partner specific for the analyte conjugate.

When a sample containing analyte is introduced into the liquid flow channel, the analyte in the sample binds to the mobile, labeled first binding partner in the first reagent reservoir, thereby preventing the labeled first binding partner from binding to the analvte conjugate in the second reagent reservoir. The reaction mixture then flows to the detection membrane where the labeled first binding partner passes through the first detection zone and is captured at the second detection zone by the third binding partner specific for the labeled first binding partner.

A preferred sandwich immunoassay format includes a first reagent reservoir containing a mobile, unlabeled first binding partner and a second reagent reservoir containing a mobile, labeled second binding partner. Both the first and second binding partners are able to simultaneously bind the substance (analyte) to be detected. It will be recognized by those skilled in the art that the first and second binding partners may be combined together in a single reagent reservoir or contained in separate reservoirs with either binding partner being in the first or second reagent reservoir. The immunochromatographic strip for this immunoassay format includes two zones comprising the following immobilized reagents: 1) a third binding partner specific for the first binding partner, and 2) a fourth binding partner specific for the labeled second binding partner.

When a sample containing analyte is introduced into the liquid flow channel, the analyte (antigen) in the sample binds to both the first and second binding partners, forning a first binding partner-analyte-labeled second binding partner complex, or sandwich. The reaction mixture then flows onto the detection membrane where the labeled complex is captured by third binding partner specific for the first binding partner in the first detection zone.

In the absence of analyte in the sample, the first binding partner-analyte-labeled second binding partner complex fails to form, and the labeled second binding partner passes through the zone containing the third binding partner and is captured and detected at the second zone containing the fourth binding partner specific for the labeled second binding partner.

From the foregoing description of assay formats, it will be apparent to one skilled in the art that the test reagents employed in the device described herein can be configured in a very wide variety of sandwich and competition immunoassay formats that have been previously described. The present assay device and immunoassay formats overcome the limitations of existing immunochromatographic or lateral flow formats by performing all or some of the critical immunochemical reactions outside of the detection membrane under the precise control of the geometries of the fluid flow channel. Unlike existing immunochromatographic and lateral flow formats and devices, which teach that simplicity and ease-of-use are gained by incorporating more and more test components onto the test strip, the present device strives to remove the critical immunochemical reactions from the test strip and to use the precisely controlled dimensions of the device to effect many complicated steps in a simple, one-step operation. The removal of the critical test reagents and reactions from the test strip, in contrast to the current teachings in the art, yields the surprising finding that the method is simpler and easier to perform, while giving more accurate and precise results.

Reagent Sink

A reagent sink is optionally included in the assay device at the distal end or downstream of the immunochromatographic membrane or strip for enhancing the flow of the fluids, including the fluid source, reagents and sample along the longitudinal length of the strip. The sink may be composed of an absorbent material, such as blotting paper, as described above with reference to the sample sink. Preferably, the sink is a further continuation of the fluid flow channel and is composed of a capillary channel segment or a defined volume that wicks or attracts liquid in the immunochromatographic strip, thereby pulling the liquids away from the strip and toward the distal end of the assay device.

End of Test Indicator

Optionally included in flow communication with the distal end of the strip is an end of test indicator for indicating completion of the assay and ensuring that the device performed correctly. The end of test indicator may be included in the reagent sink described above or may be a separate component located at the distal end, or downstream, of the immunochromatographic strip or reagent sink, if present.

The end of test indicator is preferably composed of an absorbent material containing an indicator, dye or colored particle that travels with the liquid to indicate that the liquid has traveled to the distal end of the assay device and that the assay is complete and ready for analysis. Analysis can be conducted either by visual inspection or with the aid of instrumentation. Preferably, movement of the dye through the absorbent material to a predetermined location, such as an observation window in the assay device housing, is visually detectable.

Method of Manufacture

The assay device is manufactured in such a way, such as, for example, by injection molding of plastic or laser etching of silicon, that the device has precisely controlled geometry, structure, dimensions and other features that impart precision, uniformity and reproducibility to an assay performed using the device. Such attributes are lacking in conventional onestep assay devices, which employ only membranes or other fibrous materials that function simultaneously as the reagent reservoir, reagent-analyte reaction medium and detection zone.

Preferably, the assay device is manufactured from plastic using rapid prototyping techniques or by molding two or more segments of the housing with indentations and grooves so that, when the segments of housing are assembled, the indentations and grooves coincide to form the fluid flow channels and reservoirs. The sample valve and immunochromatographic strip are prefabricated as individual components and placed on a preferred segment of housing prior to assembly so that the components become permanently secured within the housing when assembled. Alternatively, the fluid flow channel is preformed by fusing capillary channels to non-capillary channels or vessels, attaching the sample valve and immunochromatographic strip to the fluid flow channel, and molding or assembling the housing around the preformed components.

The buffer and reagents are preferably added to the immunochromatographic strip and reagent reservoirs prior to assembly. Reagents intended to be stored in a lyophilized or dried state within the assay device are applied to a predetermined location of the liquid flow channel as a liquid and are then lyophilized or allowed to dry prior to assembly of the housing and enclosure of the liquid flow channel. The reagents can be delivered to the reagent reservoir at a volume ranging from 1 to 50 $\mu L$, preferably 10 $\mu L$, in a buffer.

Assay Method

An assay is performed for the detection of analyte in a sample using the assay device described herein, with reference to the figures, as follows:

A sample is collected or obtained using methods well known to those skilled in the art. The sample containing the analyte to be detected may be obtained from any biological or environmental source and is preferably a fluid. For example, the sample may be a biological fluid, such as whole blood, blood serum, blood plasma, urine, spinal fluid, fermentation fluid, lymph fluid, tissue culture fluid and ascites fluid; any plant tissue or extract including root, stem, leaf, or seed; industrial, agricultural or chemical effluent, process stream, reaction mixture or finished product; or an environmental material such as water, including water from oceans, lakes, rivers, streams, ponds, aquifers, and wetlands; soil; sediment; sludge; or air. Preferably, the analyte in the sample is solubilized in an aqueous medium. The sample may be extracted, diluted, purified, concentrated, filtered, dissolved, suspended or otherwise manipulated prior to assay to optimize the assay results.

Analytes to be detected using the assay method described herein include, but are not limited to, the following analytes: molecules, such as organic and inorganic molecules, peptides, proteins, glycoproteins, carbohydrates, polysaccharides, nucleic acids, lipids, metal salts, ions, polymers used for water treatment, and the like. Analytes also include but are not limited to pharmaceutical drugs, drugs or substances of abuse, neurotransmitters, hormones, growth factors, antineoplastic agents, cytokines, monokines, lymphokines, nutrients, enzymes, receptors, antibacterial agents, antiviral agents, antifungal agents, and antineoplastic agents. Typical antineoplastic agents include, but are not limited to, antimetabolites such as folate antagonist, methotrexate, purine antagonist 6-mercaptopurine, pyrimidine antagonist 5-fluorouracil, cytarabine; alkylating agents such as mechlorethamine, chlorambucil, cyclophosphamide, melphalan, ifosfamide; plant alkaloids such as vincas, vinblastine, vincristine, colchicine, podophyllotoxins etoposide; antibiotics such as doxorubicin, bleomycin, mitomycin; nitrosureas such as carmustine, lomustine; inorganic ions such as cisplatin; substances such as taxol and metalloproteinase inhibitors; protease inhibitors; and hormones such as tamoxifen, and glutamide. The term analyte also means detectable components of structured elements such as cells, including all animal and plant cells, especially stem cells and blood cells, and microorganisms, such as fungi, viruses, bacteria including but not limited to all gram positive and gram negative bacteria, and protozoa. The term analyte also means detectable components of organelles and cells.

The assays are useful for diagnosing, monitoring, or evaluating conditions including, but not limited to, the evaluation of known or suspected diabetic patients (glucose, insulin, somatostatin, glucagon, growth hormone, and other molecules); determination of ovulation or pregnancy; determination of tolerance to drug toxicity or allergy; evaluation of circulating levels of pharmaceutical drug; detection of circulating levels of drugs of abuse; cardiovascular function (triglycerides, cholesterol, high density lipoprotein, low density lipoprotein, lipoprotein A (Lp(a)), lipids, and other molecules); evaluation of circulating forms of cardiac muscle proteins and other molecules that are associated with a heart attack; evaluation of immune function (cytokines, lymphokines, monokines, thymosins, adrenocorticotrophic hormone, glucocorticoids, prolactin, growth factors, tumor necrosis factor, and other molecules); evaluation of hormone levels, such as in patients with delayed or precocious puberty (luteinizing hormone releasing hormone, follicle stimulating hormone, luteinizing hormone, inhibin, estrogen and related sex steroids, testosterone and related sex steroids, progesterone, and other molecules); evaluation of growth in patients of short stature (analysis of growth hormone, somatomedins, growth factors, growth hormone releasing hormone, thyroid hormones, adrenal steroids, somatostatin, anabolic steroids and other molecules); adrenal gland dysfunction (glucocorticoids, dehydroepiandrosterone, aldosterone, deoxycortisol, corticosteroid, hydroxyprogesterone and other sex steroids, adrenocorticotropin, corticotropin releasing hormone and other peptides, catecholamines (norepinephrine and epinephrine), renin, opioids, and other molecules); thyroid gland function (thyroxine, triiodothyronines, thyroid stimulating hormone, thyrotropin releasing hormone, and other molecules); parathyroid gland function (parathyroid hormone, calcitonin, phosphorus, calcium and other molecules); kidney function and water balance (vasopressin (antidiuretic hormone), renin, aldosterone, atrial natriuretic hormone, sodium, potassium, creatinine, ammonia, calcium, and other molecules); evaluation of pancreatic endocrine function (somatostatin, glucagon, insulin, pancreatic polypeptide, amyloid and other molecules); evaluation of hypothalamic function (luteinizing hormone releasing hormone, vasopressin, oxytocin, somatostatin, thyroid hormone releasing hormone, growth hormone releasing hormone, opioids, neuropeptide Y, cholecystokinin, corticotropin releasing hormone, neurotensin, vasoactive intestinal peptide, peptide histidine isoleucine, gastrin, substance P, dopamine, norepinephrine, serotonin and other molecules); evaluation of pituitary function (growth hormone, luteinizing hormone, follicle stimulating hormone, thyroid stimulating hormone, adrenocorticotrophic hormone, prolactin, vasopressin, proopiomelanocortin and fragments thereof, oxytocin, and other molecules); evaluation of rejection following transplantation of biological or synthetic material into a patient (cytokines, lymphokines, monokines, and other factors of the immune system indicative of the occurrence of rejection); evaluation of the types and amount of bacteria, including but not limited to all gram positive and gram negative bacteria, viruses, parasites and fungi present in a sample (films coated with antibodies specific for unique epitopes on specific bacteria, viruses, parasites and fungi); evaluation of the presence and amount of molecules associated with specific cancers; evaluation of the presence and amount of variants of molecules such as apolipoprotein E that might be associated with the onset of neurological diseases such as Alzheimer's disease; and evaluation of environmental samples of water, air, plants and earth for the presence of analytes, including, but not limited to bacteria, fungi, parasites, viruses, pollutants, toxins, heavy metals, organic and inorganic molecules, additives or ingredients of foods, cosmetics or pharmaceuticals, or other manufactured, processed or finished products.

With reference to the embodiment shown in FIG. 1, a liquid sample is delivered to the sample well 10 of the sample delivery means 20 on the assay device 30 and allowed to flow into the sample capillary tube 40 contained within the sample delivery means, which is a valve. The valve is manually rotated to place the capillary tube in fluid contact with the liquid flow channel of the assay device. In the preferred embodiment of the assay method shown in FIG. 1, an air pump 50 is used to initiate the flow of a buffer, from a buffer channel reservoir 60. The buffer passes through a first reagent channel reservoir 70, preferably a capillary segment of the liquid flow channel containing first lyophilized reagent, upstream from the sample delivery valve but downstream from the buffer reservoir, and solubilizes the lyophilized reagent contained therein. The reagent is a first binding molecule having immunological specificity for the analyte, such as an antibody. The reagent is preferably unlabeled and unconjugated to a solid phase bead or particle and is soluble in the buffer. Most preferably, the first binding molecule is an antibody, such as a mouse antibody, that is captured by an antimouse antibody immobilized on the detection membrane as described in more detail below.

The buffer and solubilized reagent then pass through the capillary segment 40 of the sample delivery valve 20 to interact with the analyte in the sample. After passing through the sample valve, the buffer, first binding molecule and sample flow into one or more mixing chambers 80 to enable the first binding molecule and sample to intermix, thereby promoting binding between analyte present in the sample and the first binding molecule to form an analyte-first binding molecule complex.

The solution containing the analyte, first binding molecule and buffer then flows into a second reagent channel reservoir 90 containing a second reagent, preferably a lyophilized, labeled or particle-conjugated binding molecule specific for either the first binding molecule or the analyte, thereby reconstituting the second lyophilized reagent. Preferably, the second reagent is particle-conjugated analyte that competes with analyte in the sample for the first binding molecule. The solution then flows into one or more second mixing chambers 100 to permit mixing of the analyte-first binding molecule complex with the second reagent.

The solution mixture then flows through a porous, separating membrane 105 that retains reagents bound to particles unable to pass through the pores of the membrane, such as antibody bound to the particle-conjugated analyte. Fluid passing through the membrane passes through a third reagent channel reservoir, preferably containing a diffusable, labeled third binding molecule that binds to the first binding molecule 110, followed by a third set of mixing chambers 115 and is then delivered onto an immunochromatographic membrane or strip 120, which is in flow communication with the third mixing chamber 115 of the liquid flow channel. Preferably, the third binding molecule is an antimouse antibody immobilized on gold or otherwise colored particles. The immunochromatographic strip 120 contains one or more reagents deposited thereon for the detection of analyte, such as an immobilized binding partner specific for the first binding partner, analyte, the analyte-first binding molecule complex, the second binding molecule or any combinations or complexes thereof.

The immunochromatographic strip 120 is in fluid communication with a sink 125 that attracts fluids from the strip to an end-of-test indicator 130. The solution mixture flows from the immunochromatographic strip 120 to the end-of-test indicator 130 containing a dried dye. The solution solubilizes the dye, which migrates with the solution mixture to the distal end of the liquid flow channel where the dye is visually detected through a window in the housing (not shown) that encases the liquid flow channel. Detection of the dye in the window indicates completion of the assay.

With reference to FIG. 2, a liquid sample is delivered to the sample well 150 of a sample valve 160 on the assay device 170 and allowed to flow through a separating membrane 175 into the sample capillary tube 180 contained within the sample valve. The flow of the sample into the sample capillary tube is encouraged by a sample sink 185 opposite the sample well. The valve is manually rotated to place the capillary tube in fluid contact with the liquid flow channel of the assay device. In the preferred embodiment of the assay device shown in FIG. 2, the action of rotating the capillary tube into alignment with the liquid flow channel initiates the flow of assay buffer from a buffer reservoir 190. The buffer passes through a first reagent channel reservoir 200, preferably a capillary segment of the liquid flow channel containing first lyophilized reagent, upstream from the sample delivery valve but downstream from the buffer reservoir, and solubilizes the lyophilized reagent contained therein. The reagent is preferably a first binding molecule having immunological specificity for the analyte, such as an antibody. The reagent is preferably unlabeled and unconjugated to a solid phase bead or particle and is soluble in the buffer.

The buffer and solubilized reagent then pass through the capillary segment 180 of the sample delivery valve 160 to interact with the analyte in the sample. After passing through the sample valve, the buffer, first reagent and sample flow into a second reagent channel reservoir 205 containing a second reagent, preferably a lyophilized, labeled or particle-conjugated binding molecule specific for either the first binding molecule or the analyte, thereby reconstituting the second lyophilized reagent.

The solution mixture then flows onto an immunochromatographic membrane or strip 210, which is in flow communication with the second reagent channel reservoir 205 of the liquid flow channel. The immunochromatographic strip 210 contains one or more reagents deposited thereon for the detection of analyte, such as an immobilized binding partner specific for the first binding partner, analyte, the analyte-first binding molecule complex, the second binding molecule or any combinations or complexes thereof.

The immunochromatographic strip 210 is in fluid communication with a capillary sink 220 that attracts fluids from the strip to an end-of-test indicator 230. The solution mixture flows from the immunochromatographic strip 210 to the end-of-test indicator 230 containing a lyophilized dye. The solution solubilizes the dye, which migrates with the solution mixture to the distal end of the liquid flow channel where the dye is visually detected through a window 240 in the housing (not shown) that encases the liquid flow channel. Detection of the dye in the window indicates completion of the assay.

With reference to FIG. 3, a liquid sample is delivered to the sample well 310 of a sample valve 320 on the assay device 330 and allowed to flow into the sample capillary tube 340 contained within a sample valve. The valve is manually rotated to place the capillary tube in fluid contact with the liquid flow channel of the assay device. In the preferred embodiment of the assay method, the action of rotating the capillary tube into alignment with the liquid flow channel initiates the flow of an assay buffer, from a reservoir 360. The buffer passes through a first reagent channel reservoir 370, preferably a capillary segment of the liquid flow channel containing a first lyophilized reagent, upstream from the sample delivery valve but downstream from the buffer reservoir, and solubilizes the lyophilized reagent contained therein. The reagent is a first binding molecule having immunological specificity for the analyte, such as an antibody. The reagent is preferably unlabeled and unconjugated to a solid phase bead or particle and is soluble in the buffer.

The buffer and solubilized reagent then pass through the capillary segment 340 of the sample delivery valve 320 to interact with the analyte in the sample. After passing through the sample valve, the buffer, first binding molecule and sample flow into a mixing chamber 380 to enable the first binding molecule and sample to intermix, thereby promoting binding between analyte present in the sample and the first binding molecule to form an analyte-first binding molecule complex.

The solution containing the analyte, first binding molecule and buffer then flows into a second reagent channel reservoir 390 containing a second reagent, preferably a lyophilized, labeled or particle-conjugated binding molecule specific for either the first binding molecule or the analyte, thereby reconstituting the second lyophilized reagent. The solution then flows into a second mixing chamber 400 to permit mixing of the analyte-first binding molecule complex with the second binding molecule.

The solution mixture then flows onto an immunochromatographic membrane or strip 410, which is in flow communication with the second mixing chamber 400 of the liquid flow channel. The immunochromatographic strip 410 contains one or more reagents deposited thereon for the detection of analyte, such as an immobilized binding partner specific for the first binding partner, analyte, the analyte-first binding molecule complex. the second binding molecule or any combinations or complexes thereof.

The immunochromatographic strip 410 is in fluid communication with an end-of-test indicator 420. The solution mixture flows from the immunochromatographic strip 410 to the end-of-test indicator 420 containing a lyophilized dye. The solution solubilizes the dye, which migrates with the solution mixture to the distal end of the liquid flow channel where the dye is visually detected through a window in the housing 430 that encases the liquid flow channel. Detection of the dye in the window indicates completion of the assay.

With reference to FIG. 4, a liquid sample is delivered to a sample well 510 of a sample valve 520 on the assay device 530 and allowed to flow into the sample capillary tube 540 contained within the sample valve. The valve is manually rotated to place the capillary tube in fluid contact with the liquid flow channel of the assay device. In the preferred embodiment of the assay method, the action of rotating the capillary tube into alignment with the liquid flow channel initiates the flow of buffer, from a buffer reservoir 550.

The buffer passes through the capillary segment 540 of the sample delivery valve 520 to interact with the analyte in the sample. After passing through the sample valve, the buffer and sample flow into a first reagent channel reservoir 570, preferably a capillary segment of the liquid flow channel containing first lyophilized reagent and solubilizes the lyophilized reagent contained therein. The reagent is a first binding molecule having immunological specificity for the analyte, such as an antibody. The reagent is preferably unlabeled and unconjugated to a solid phase bead or particle and is soluble in the buffer.

The solution containing the analyte, first binding molecule and buffer then flows into a second reagent channel reservoir 590 containing a second reagent, preferably a lyophilized, labeled analyte, such as analyte-coated gold, thereby reconstituting the second lyophilized reagent. The solution then flows into a mixing chamber 600 to permit mixing of the analyte, first reagent, and second reagent. In the mixing chamber, the three components, most preferably analyte, an anti-analyte binding molecule, and labeled analyte, react and come to substantial equilibrium.

The solution mixture then flows onto an immunochromatographic membrane or strip 610, which is in flow communication with the mixing chamber 600 of the liquid flow channel. The immunochromatographic strip 610 contains one or more reagents deposited thereon for the detection of analyte, such as immobilized binding partner specific for the first binding partner, analyte, the analyte-first binding molecule complex, the second binding molecule or any combinations or complexes thereof. The reagents are preferably deposited in separate zones 620 for subsequent visual detection of labeled reactants. Preferably, the first zone of the strip contains immobilized anti-mouse antibody specific for the first binding molecule and the second zone of the strip contains an immobilized antibody specific for the label with which the analyte or second binding molecule is labeled.

The immunochromatographic strip 610 is in fluid communication with an end-of-test indicator 630. The solution mixture flows from the immunochromatographic strip 610 to the end-of-test indicator 630 containing a lyophilized dye. The solution solubilizes the dye, which migrates with the solution mixture to the distal end of the liquid flow channel where the dye is visually detected through a window in the housing 640 that encases the liquid flow channel. Detection of the dye in the window indicates completion of the assay.

In a most preferred embodiment of the assay method using the device shown in FIG. 4, the first reagent is uncoupled, unlabeled anti-analyte antibody and the second reagent is a particle that has been coated with both analyte and a ligand that is bound by the immobilized binding partner located in the second zone of the detection membrane. For example, the particle is a gold particle coated with analyte and bovine serum albumin (BSA) and the immobilized binding partner is an anti-BSA antibody. The preferred gold particle is a colloidal gold particle ranging in diameter from 5 to 80 nm, most preferably 20 nm.

In the most preferred embodiment, when sample is delivered to the liquid flow channel, buffer is released from the buffer reservoir and flows with the sample to the first reagent reservoir where the lyophilized anti-analyte antibody is reconstituted. The reaction mixture then flows along the liquid flow channel, incubating for a precise period of time, depending on the dimensions of the capillary channel. The buffer, sample and first reagent reaction mixture then flows to the second reagent reservoir where the lyophilized analytecoated gold particles are reconstituted. The reaction mixture then enters the mixing chamber having a geometry and structural features that cause turbulent flow, promote mixing, and provide for a precise incubation time. It will be understood by those skilled in the art that the order of the reagents may be reversed or the reagents may be combined, depending on the configuration of the particular assay employed.

The design of the assay device channels and chambers are such that the antigen-specific immunochemical reaction occurs and substantially reaches equilibrium prior to contacting the detection strip. The reaction mixture then contacts the detection strip. Fluid flow through the strip is caused by capillary action. The reaction mixture passes through the first zone of the detection strip, which contains an immobilized binding molecule specific for the first reagent, such as anti-mouse antibody, and the first binding molecule is bound. It will be understood by those skilled in the art that the first binding molecule could be an antibody from any species and the immobilized binding molecule could then be reactive with antibodies from any other species of animals. The antibodies can be monoclonal or polyclonal or immunoreactive antibody fragments. The reaction mixture continues its flow toward the distal end of the detection strip and contacts and reacts with the second zone, which contains an anti-ligand binding molecule, and the labeled particle is bound. A mobile dye, soluble in the reaction mixture, is carried along with the fluid flow to the distal end of the detection strip where, when the flow stops, the dye is visible through a window in the assay device housing, indicating completion of the assay.

In the most preferred embodiment, when analyte is present in the sample, the analyte and first binding molecule (preferably an anti-analyte antibody) form a complex and the first binding molecule is prevented from binding to the second reagent (analyte-coated, detectable particle, such as a colored or gold particle). Therefore, the analyte-coated, detectable particle passes through the first zone of the detection membrane and is bound at the second zone (for example, an immobilized anti-BSA antibody binds to BSA, with which the particle is coated). When analyte is not present in the sample, the first binding molecule (preferably an anti-analyte antibody) binds to the analyte-coated, detectable particle which, in turn, is bound by the immobilized binding molecule in the first zone of the detection membrane. To summarize, if analyte is present in the sample, a visual signal is detected in the second zone of the immunochromatographic strip, whereas if analyte is not present in the sample, a visual signal is detected in the first zone of the immunochromatographic strip.

It is contemplated within the scope of the assay device described herein that the configuration of reagents on the detection strip can be such that only one of the two zones has visually detectable color or that both zones may have color and that the degree of color intensity, when compared with each other is an indicator of analyte concentration.

The assay device, methods of use and manufacture, and immunoassay formats described above will be further understood with reference to the following non-limiting examples.

EXAMPLE 1

Detection of Polychlorinated Biphenyls (PCBs) in Water Using an Integrated Immunoassay Device This example illustrates the use of the integrated immunoassay device described herein to detect PCBs in a water sample.

The immunoassay device used in this example provides for all of the manipulations commonly required in an immunochromatographic strip assay, including the filtration of sample, the subsequent measurement of a discrete sample volume from the filtered sample and the introduction of sample into the flow path of the assay. The immunoassay device also contains all reagents, an immunochromatographic strip, and buffers required to complete the immunoassay after applying the sample to the device.

The device is a liquid flow channel in which fluids move from the proximal to the distal end. The liquid flow channel is in fluid communication with the following five primary sections: a buffer reservoir; sample well and valve assembly; a reagent reservoir; a mixing chamber, and an immunochromatographic strip. The device was prepared as follows.

Materials and Methods

Sink Pad

A cellulosic filter pad (Ahlstrom Filtration, Mt. Holly Springs, Pa.) was cut to a 0.65×2.5 cm size. A band of a 0.5 mg/mL solution of blue dye was applied to the pad at a concentration of 1.8 $\mu$L per pad. The pad was dried at 37° C. for two hours.

Monoclonal Antibody-gold Conjugate Production 100 mL of 20 nm diameter gold sol (BBI International, Cardiff, United Kingdom) was combined with 1 mg of an anti-PCB monoclonal antibody (TSD Bioservices, Newark, Del.) and incubated for 15 minutes, centrifuged and decanted. The pellet was resuspended in phosphate buffered saline (PBS) containing 2% bovine serum albumin (BSA).

Immunochromatographic Strip

A nitrocellulose membrane (approximately 12 µm pore diameter) was cut into a 0.65×3 cm strip. A PCB-protein conjugate was applied to the strip at a concentration of approximately 1 mg/mL in a band across the proximal end of the membrane at a volume of 0.65 µL per test.

Goat anti-mouse antibody was applied at a concentration of approximately 5 mg/mL in a band across the distal end of the strip at a volume of 0.65 µL per test. The strip was dried at 37° C. for one hour. The membrane was applied to a 0.65×5.3 cm adhesive-backed mylar sheet, leaving 2.3 cm of exposed adhesive-coated mylar at the distal end of the strip. The 0.65×2.5 cm cellulosic sink pad described above was applied to the exposed adhesive so that the sink pad overlapped the membrane by 2 mm.

Immunochromatographic Device Preparation

Ten microliters of a 1 OD/mL solution of the monoclonal antibody-gold conjugate, described above, was applied to a reagent reservoir in the unassembled device. The device was frozen and the reagent lyophilized. Following lyophilization, the device was assembled by placing the immunochromatographic strip, described above, into the device, sonically welding the cover into place, adding 250 µL of an assay buffer containing between 0.05 and 1% surfactant in phosphate buffered saline to the buffer reservoir, upstream from the sample well inlet, foil sealing the buffer reservoir, and securing a glass fiber filter pad in the sample well.

PCB Assay Procedure

A deionized water sample, containing various concentrations of AROCHLOR™ 1254 polychlorinated biphenyl (PCB) (Chem Services, West Chester, Pa.) was placed in the sample well of the integrated immunoassay device. The filtered sample flowed into a predefined volume sample capillary, and the sample valve was rotated 90 degrees to align the sample capillary with the flow path of the liquid flow channel of the device. The turning of the valve broke the communication between the sample contained in the well and the sample capillary, thereby eliminating the possibility of overdosing the system. The turning of the valve also brought the sample in the sample capillary into fluid communication with the liquid flow channel and released the assay buffer from the buffer reservoir (upstream) into the liquid flow channel. As sample is pulled into the capillary channel from the sample capillary, the buffer follows immediately behind.

The buffer reservoir is a ridged, back filled, foil sealed compartment containing 1.2 mL of buffer. Once the foil seal has been applied, the buffer remains in the reservoir until the valve has been turned to the flow path position. As the valve is turned to initiate flow into the flow path, the buffer reservoir becomes vented to the outside, allowing buffer to freely flow into the device under atmospheric pressure.

The assay buffer and sample flowed downstream to the monoclonal antibody-gold conjugate reagent, which was contained in a lyophilized state in the reagent reservoir. As the sample and buffer flowed through the reagent reservoir, they rehydrated the lyophilized reagent which had been previously deposited. The rehydrated reagent reacted with the sample and flowed into the mixing chamber. When the mixing chamber was full, the reaction mixture, containing the buffer, sample, and reagent, flowed onto the immunochromatographic strip. As the components migrated along the strip toward the distal end, they were captured and deposited as bands in specific zones on the strip. The housing of the device contained windows through which the zones and an end-of-test indicator were visually observed. The remainder of the housing was opaque.

Sample filtration occurred as the sample was applied to the sample well, below which was mounted a 7.5 mm glass fiber filter disk. The sample readily moved into the sample capillary underlying the filtration media by gravitational force. The sample capillary has a total volume capacity of 10 µL. The sample capillary is part of a rotating valve assembly which is vented to the outside of the device to promote flow of the sample into the sample capillary. After the sample capillary was filled with sample, the valve was turned to a set point which aligned the sample capillary with the flow path of the liquid flow channel of the device. As sample was pulled into the capillary channel from the sample capillary, the buffer reservoir became vented to the outside, allowing buffer to freely flow into the liquid flow channel of the device under atmospheric pressure.

When PCB was absent from the sample, the monoclonal antibody-gold conjugate from the reagent reservoir was bound by the PCB-protein conjugate immobilized on the immunochromatographic strip. When PCB was present in the sample, the sample PCB became bound to the monoclonal antibody-gold conjugate from the reagent reservoir, thereby preventing or reducing the binding of the monoclonal antibody-gold conjugate from the reagent reservoir to the PCB-protein conjugate immobilized on the immunochromatographic strip. The PCB-monoclonal antibody-gold conjugate complex was then captured by the goat anti-mouse antibody immobilized on the strip. Therefore, as the concentration of PCB in the sample increased there was a proportional displacement of the monoclonal antibody-gold conjugate from the PCB-protein conjugate zone to the subsequent goat anti-mouse zone, where it was visualized.

As the assay progressed, the dye in the sink pad moved to the distal end of the strip with the buffer front. A window in the housing above the distal end of the strip provided visual access to this area of the strip. Visualization of the dye through the window indicated the completion of the immunoassay. The entire test from sample application to result readout required between approximately 15 and 20 minutes.

EXAMPLE 2

Detection of Mouse IgG in Hybridoma Cell Supernatants Using an Integrated Immunoassay Device This example illustrates the use of the integrated immunoassay device described herein, in a sandwich immunoassay format, to detect mouse IgG in a hybridoma cell supernatant sample.

The device is similar to the device described above in Example 2 and was prepared as follows.

Materials and Methods

Sink Pad

The sink pad was prepared as described above in Example 2.

Monoclonal Antibody-gold Conjugate Production 100 mL of 20 nm diameter gold sol (BBI International, Cardiff, United Kingdom) was combined with 1 mg of a donkey anti-mouse antibody (Rockland, Gilbertsville, Pa.) and incubated for 15 minutes to form a gold-donkey anti-mouse antibody complex. The reaction mixture was centrifuged and decanted. The pellet, containing the gold-donkey anti-mouse antibody complex was resuspended in phosphate buffered saline (PBS) containing 2% bovine serum albumin (BSA).

Immunochromatographic Strip

A nitrocellulose membrane (approximately 12 μm pore diameter) was cut into a 0.65×3 cm strip.

Donkey anti-mouse antibody was applied to the strip at a concentration of 1 mg/mL in a band across the proximal end of the membrane at a volume of 0.65 μL.

An anti-gold reagent, the Goldline2™ reagent (BBI International), was applied to each strip at a concentration of approximately 1 mg/mL in a band across the distal end of the membrane at a concentration of 0.65 μL per membrane strip. The strip was then dried at 37° C. for one hour.

The membrane strip was applied to a 0.65×5.3 cm adhesive-backed mylar sheet, leaving 2.3 cm of exposed adhesive-coated mylar at the distal end of the strip. The 0.65×2.5 cm cellulosic sink pad described above was applied to the exposed adhesive so that the sink pad overlapped the membrane by 2 mm.

Immunochromatographic Device Preparation

10 μl of a 1 OD/mL solution of the donkey anti-mouse-gold conjugate complex, described above, was applied to a reagent reservoir in the unassembled device. The device was frozen and the reagent lyophilized. Following lyophilization, the device was assembled by placing the immunochromatographic strip, described above, into the device, sonically welding the cover into place, adding 250 μL of an assay buffer containing between 0.05 and 1% surfactant in phosphate buffered saline to the buffer reservoir, upstream from the sample well inlet, foil sealing the buffer reservoir, and securing a glass fiber filter pad in the sample well.

Assay Procedure

Hybridoma cell supernatants containing various concentrations of mouse monoclonal antibody were applied to the sample well of each immunoassay device, described above. The samples were permitted to soak into the glass fiber filter pad in the sample well for 30 seconds. The sample valve was rotated 90 degrees. The turning of the valve broke the communication between the sample contained in the well and the sample capillary, thereby eliminating the possibility of overdosing the system. The turning of the valve brought the sample in the sample capillary into fluid communication with the liquid flow channel and released the assay buffer (upstream) into the liquid flow channel.

The assay buffer and sample flowed downstream to the donkey anti-mouse-gold conjugate complex reagent, which was contained in a lyophilized state in the reagent reservoir. As the sample and buffer flowed through the reagent reservoir, they rehydrated the lyophilized reagent which had been previously deposited. The rehydrated reagent reacted with the sample and flowed into the mixing chamber. When the mixing chamber was full, the reaction mixture, containing the buffer, sample, and reagent, flowed onto the immunochromatographic strip. As the components migrated along the strip toward the distal end, they were captured and deposited as bands in specific zones on the strip. The housing of the device contained windows through which the zones and an end-of-test indicator were visually observed when the test indicator window turned blue due to the presence of the dye. The remainder of the housing was opaque.

Sample filtration and liquid fluid flow occurred as described in Example 1.

When mouse IgG was absent from the sample, the donkey anti-mouse-gold conjugate complex reagent from the reagent reservoir was bound by the anti-gold antibody immobilized at the distal end of the immunochromatographic strip. When mouse IgG was present in the sample, the sample mouse IgG became bound to the donkey anti-mouse-gold conjugate complex from the reagent reservoir. This complex then bound to the donkey anti-mouse-gold conjugate immobilized at the proximal end of the immunochromatographic strip. Therefore, as the concentration of mouse IgG in the sample increased there was a proportional increase in the amount of complex at the donkey anti-mouse zone with a corresponding decrease in complex formation at the anti-gold zone.

As the assay progressed, the dye in the sink pad moved to the distal end of the strip with the buffer front. A window in the housing above the distal end of the strip provided visual access to this area of the strip. Visualization of the dye through the window indicated the completion of the immunoassay. The entire test from sample application to result readout required approximately 10 minutes.

Samples containing greater than 1 μg/mL produced a positive test result. Samples containing less than 0.5 μg/mL produced a negative test result.

EXAMPLE 3

Detection of a Pharmaceutical Drug in Human Plasma Using an Integrated Immunoassay Device This example illustrates the use of the integrated immunoassay device described herein to detect a small molecular weight pharmaceutical drug in a human plasma sample.

The device was similar to the device described above in Example 2 and was prepared as follows.

Materials and Methods

Sink Pad

The sink pad was prepared as described in Example 2.

Gold-antibody Conjugate Production 100 mL of 20 nm diameter gold sol (BBI International, Cardiff, United Kingdom) was combined with 1 mg of a small molecular weight pharmaceutical drug-goat IgG antibody conjugate and was incubated for 15 minutes to form a gold-drug-goat IgG antibody conjugate complex. The reaction mixture was centrifuged and decanted. The pellet, containing the gold-antibody complex was resuspended in phosphate buffered saline (PBS) containing 2% bovine serum albumin (BSA).

Immunochromatographic Strip

The immunochromatographic strip was composed of a nitrocellulose membrane matrix, an absorbent wicking material, and an adhesive backing to hold the unit together.

A nitrocellulose membrane (approximately 12 μm pore diameter) was cut into a 0.65×3 cm strip.

Donkey anti-mouse antibody was applied to the strip at a concentration of 1 mg/mL in a band across the proximal end of the membrane at a concentration of 0.65 μL.

Rabbit anti-goat antibody was applied to each strip at a concentration of approximately 2 mg/mL in a band across the distal end of the membrane at a concentration of 0.65 μL per membrane strip. The strip was then dried at 37° C. for one hour. The spacing of the reagent application zones allowed for the discrete application and drying of each reagent during assembly of the immunoassay device.

The membrane strip was applied to a 0.65×5.3 cm adhesive-backed mylar sheet, leaving 2.3 cm of exposed adhesive-coated mylar at the distal end of the strip. The 0.65×2.5 cm cellulosic sink pad described above was applied to the exposed adhesive so that the sink pad overlapped the membrane by 2 mm.

Immunochromatographic Device Preparation

Ten microliters of a 1 μg/mL mouse monoclonal anti-drug antibody was applied to a first reagent reservoir in the unassembled device. 10 μl of a 1 OD/nL solution of the gold-drug-goat IgG conjugate complex was applied to a second reagent reservoir in the device downstream from the first reagent reservoir. The device was frozen and the reagents were lyophilized. Following lyophilization, the device was assembled by placing the immunochromatographic strip, described above, into the device, sonically welding the cover into place, adding 250 μL of an assay buffer containing between 0.05 and 1% surfactant in phosphate buffered saline to the buffer reservoir, upstream from the sample well inlet, foil sealing the buffer reservoir, and securing a glass fiber filter pad in the sample well.

Assay Procedure

Whole blood samples containing various concentrations of the small molecular weight pharmaceutical drug were applied to separate devices. The samples were permitted to soak into the glass fiber filter pad in each sample well for two minutes. The sample valve was rotated 90 degrees to the "on" position. The turning of the valve breaks the communication between the sample contained in the well and the sample capillary, thereby eliminating the possibility of over-dosing the system. The turning of the valve brought the sample in the sample capillary into fluid communication with the liquid flow channel and released the assay buffer (upstream) into the liquid flow channel.

The assay buffer and sample flowed downstream to the mouse monoclonal anti-drug antibody, which was contained in a lyophilized state in the first reagent reservoir. As the sample and buffer flowed through the reagent reservoir, they rehydrated the lyophilized reagent. The rehydrated reagent reacted with the sample and flowed downstream to the gold-drug-goat IgG conjugate complex. The rehydrated reagent reacted with the other components of the fluid stream and flowed into a mixing chamber. When the mixing chamber was full, the reaction mixture, containing the buffer, sample, and reagents, flowed onto the immunochromatographic strip. As the components migrated along the strip toward the distal end, they were captured and deposited as bands in specific zones on the strip. The housing of the device contains windows through which the zones and an end-of-test indicator were visually observed when the test indicator window turns blue due to the presence of the dye. The remainder of the housing is opaque.

Sample filtration and liquid fluid flow occur as described in Example 1.

When drug was absent from the sample, the mouse antidrug monoclonal antibody from the first reagent reservoir bound to the gold-drug-goat IgG complex from the second reagent reservoir. This complex was bound to the donkey anti-mouse antibody immobilized at the proximal end of the immunochromatographic strip. When drug was present in the sample, the mouse anti-drug monoclonal antibody from the first reagent reservoir bound to the drug in the sample. This antibody-antigen complex then became bound to the donkey anti-mouse antibody immobilized at the proximal end of the strip. The gold-drug-goat IgG migrated to the distal end of the strip where it bound to the immobilized rabbit anti-goat antibody. Therefore, as the concentration of drug in the sample increased there was a proportional displacement of the detectable complex from the donkey anti-mouse zone to the rabbit anti-goat zone.

As the assay progresses, the dye in the sink pad moves to the distal end of the strip with the buffer front. A window in the housing above the distal end of the strip provides visual access to this area of the strip. Visualization of the dye through the window indicates the completion of the immunoassay. The entire test from sample application to result readout requires approximately 10 minutes.

Samples containing greater than 25 ng/mL produced a positive test result. Samples containing less than 12.5 ng/mL produced a negative test result.

Modifications and variations of the present assay device and methods of use and manufacture will be obvious to those skilled in the art from the foregoing detailed description. Such modifications and variations are intended to come within the scope of the appended claims.

We claim:

1. An assay device for detecting an analyte in a sample, consisting of:
    a continuous liquid flow channel having a proximal end and a distal end, wherein liquid flow between the proximal end and distal end is independent of gravity, wherein the continuous liquid flow channel includes an internal cross-sectional shape comprising an acute angle for:
        promoting capillary flow within the liquid flow channel,
        regulating the flow rate through the liquid flow channel to permit a reaction in the liquid flow channel;
    a detection membrane, wherein the distal end of the liquid flow channel is in liquid flow communication with the detection membrane, wherein the detection membrane captures a product of the reaction from the liquid flow channel; and
    a sample delivery means comprising
        a sample well in which the sample is collected; and
        a capillary channel, wherein the sample well is in liquid flow communication with the capillary channel for delivering a predetermined volume of sample from the sample well to the liquid flow channel when the sample delivery means is manipulated to place the capillary channel in liquid flow communication with the liquid flow channel, wherein liquid flow of the sample is induced by a resultant capillary flow, and a reaction within the liquid flow channel is initiated by the resultant capillary flow from the sample delivery means; and
        an end of test indicator for indicating that the liquid has traveled to the distal end of the continuous liquid flow channel and the resulting reaction and detection membrane are ready for analysis.

2. The assay device of claim 1 wherein the liquid flow channel has predetermined dimensions that control the volume, reaction time, and reaction conditions of an assay.

3. The assay device of claim 1 wherein the internal cross-sectional shape is a trapezoid.

4. The assay device of claim 1 wherein the sample delivery means is a rotatable valve that is manipulated by rotation or a slidable valve that is manipulated by sliding.

5. The assay device of claim 1 wherein the sample contains cellular or particulate components and liquid components, and the sample delivery means further comprises filtration means for separating the cellular or particulate components from the sample prior to delivery of the liquid components of the sample to the liquid flow channel.

6. The assay device of claim 1 further comprising a buffer reservoir in liquid flow communication with the liquid flow channel.

7. The assay device of claim 1 further comprising an assay reagent in a reagent reservoir, wherein the reagent reservoir is in liquid flow communication with the liquid flow channel.

8. The assay device of claim 7 wherein the assay reagent is a lyophilized reagent.

9. The assay device of claim 1 wherein the liquid flow channel further comprises one or more chambers for facilitating the mixing of sample and assay reagent.

10. The assay device of claim 1 wherein the detection membrane comprises an immunochromatographic membrane upon which has been deposited an immunoreagent.

11. The assay device of claim 1 further comprising means for initiating the flow of a liquid through the liquid flow channel from the proximal end to the distal end.

12. The assay device of claim 1 wherein the sample delivery means further comprises an extraction means to separate or remove one or more components from the sample by solid phase extraction or affinity chromatography.

13. The assay device of claim 1 further comprising an end of test indicator in fluid communication with the distal end of the liquid flow channel.

14. The assay device of claim 1 further comprising a reagent separation means at the distal end of the liquid flow channel, wherein the reagent separation means retains and thereby separates reagent particles from the fluid component of a reaction mixture containing particles.

15. The assay device of claim 1 wherein the sample travels as a bolus of liquid through the liquid flow channel.

16. An assay device for detecting an analyte in a sample, consisting of:
 a) a liquid flow channel having a proximal end and a distal end, wherein liquid flow between the proximal end and distal end is independent of gravity, wherein the continuous liquid flow channel includes an internal cross-sectional shape comprising an acute angle for:
  promoting capillary flow within the liquid flow channel,
  regulating the flow rate through the liquid flow channel to permit a reaction in the liquid flow channel;
 b) an assay buffer reservoir containing an assay buffer, wherein the assay buffer reservoir is in fluid communication with the liquid flow channel;
 c) a first reagent reservoir in fluid communication with the liquid flow channel downstream from the assay buffer reservoir;
 d) a second reagent reservoir in fluid communication with the liquid flow channel downstream from both the assay buffer reservoir and the first reagent reservoir; and
 e) a detection membrane, wherein the distal end of the liquid flow channel is in liquid flow communication with the detection membrane for detection of analyte; and
 f) a sample delivery means comprising a sample well having an aperture and a capillary channel, wherein the sample delivery means is manipulated to align the capillary channel with the aperture of the sample well or to align the capillary channel with the liquid flow channel, wherein liquid flow of the sample is induced by a resultant capillary flow and a reaction within the liquid flow channel is initiated by the resultant capillary flow from the sample delivery means.

17. The assay device of claim 16 wherein the liquid flow channel has predetermined dimensions that control the volume, reaction time, and reaction conditions of an immunoassay.

18. The assay device of claim 16 wherein the internal cross-sectional shape is a trapezoid.

19. The assay device of claim 16 wherein the sample delivery means is a rotatable valve that is manipulated by rotation or a slidable valve that is manipulated by sliding.

20. The assay device of claim 16 wherein the sample contains cellular or particulate components and liquid components, and the sample delivery means further comprises filtration means for separating the cellular or particulate components from the sample prior to delivery of the liquid components of the sample to the liquid flow channel.

21. The assay device of claim 16 wherein the first and second reagent reservoirs each contain one or more reagents.

22. The assay device of claim 21 wherein one or more of the reagents are lyophilized.

23. The assay device of claim 16 wherein the liquid flow channel further comprises means for facilitating the mixing of sample and assay reagent.

24. The assay device of claim 16 further comprising means for initiating the flow of a liquid through the liquid flow channel from the proximal end to the distal end.

25. The assay device of claim 16 wherein the sample delivery means further comprises an extraction means to separate or remove one or more components from the sample by solid phase extraction or affinity chromatography.

26. The assay device of claim 16 further comprising an end of test indicator in fluid communication with the distal end of the liquid flow channel.

27. The assay device of claim 16 further comprising a reagent separation means at the distal end of the liquid flow channel, wherein the reagent separation means retains and thereby separates reagent particles from the fluid component of a reaction mixture containing particles.

28. The assay device of claim 16 wherein the sample travels as a bolus of liquid through the liquid flow channel.

29. The assay device of claim 1 further comprising a housing substantially surrounding the device, the housing comprising an inert material and at least two or more pre-shaped sections; wherein the pre-shaped sections comprise at least one area for allowing visual monitoring of the assay device.

* * * * *